(12) United States Patent
Caron et al.

(10) Patent No.: US 8,877,802 B2
(45) Date of Patent: Nov. 4, 2014

(54) ANTIPARKINSONIAN ACTION OF PHENYLISOPROPYLAMINES

(75) Inventors: Marc G. Caron, Hillsborough, NC (US); Tatyana D. Sotnikova, Chapel Hill, NC (US); Raul R. Gainetdinov, Chapel Hill, NC (US)

(73) Assignee: Duke Univerity, Durham, NC (US)

( * ) Notice: Subject to any disclaimer, the term of this patent is extended or adjusted under 35 U.S.C. 154(b) by 2413 days.

(21) Appl. No.: 11/460,046

(22) Filed: Jul. 26, 2006

(65) Prior Publication Data

US 2007/0027208 A1   Feb. 1, 2007

Related U.S. Application Data

(60) Provisional application No. 60/703,137, filed on Jul. 28, 2005.

(51) Int. Cl.
*A61K 31/36* (2006.01)
*A61K 31/135* (2006.01)
*A61K 31/137* (2006.01)

(52) U.S. Cl.
CPC ............. *A61K 31/137* (2013.01); *A61K 31/36* (2013.01)
USPC .......................................... 514/464; 514/649

(58) Field of Classification Search
CPC ............................. A61K 31/36; A61K 31/137
USPC .......................................... 514/449, 464, 649
See application file for complete search history.

(56) References Cited

U.S. PATENT DOCUMENTS

| | | |
|---|---|---|
| 3,547,999 A | 12/1970 | Shulgin et al. |
| 3,933,911 A | 1/1976 | Main |
| 4,034,113 A | 7/1977 | Shulgin |
| 4,105,695 A | 8/1978 | Partyka et al. |
| 4,758,571 A * | 7/1988 | Curtius et al. ............. 514/249 |
| 5,866,756 A | 2/1999 | Giros et al. |
| 6,218,595 B1 | 4/2001 | Giros et al. |
| 6,797,732 B2 | 9/2004 | Virkki et al. |
| 2004/0147613 A1 | 7/2004 | Dawirs |
| 2005/0059743 A1 | 3/2005 | Epstein et al. |
| 2006/0241082 A1 | 10/2006 | Fleckenstein et al. |

OTHER PUBLICATIONS

Lebsanft. MDMA ("Ecstasy") in Tiermodellen des Morbus Parkinson Universitat Tubingen, 15 Fakultat fur Biologie Oct. 27, 2004.pp. 1-2.*
STN database Registry Nov. 16, 1984,Ecstasy, 42542-10-9/rn.*
Schmidt WJ et al. Ecstasy counteracts catalepsy in rats, an antiparkinsonian effect? Neuroscience Letters. 2002; 330: 251-254.
Lebsanft HB et al. 3.4-methylenedioxymethamphetamine counteracts akinesia enantioselectively in rat rotational behavior and catalepsy. Synapse. 2005; 55: 148-155.
Sotnikova TD et al. DDD mice, a novel acute mouse model of Parkinson's disease. Neurology. 2006; 67: S12-S17.
International Search Report for PCT/US 05/29096, Aug. 3, 2007.
Parkes, J D, et al., Amphetamines in the treatment of Parkinson's disease, Journal of Neurology, Neurosurgery, and Psychiatry (1975), pp. 232-237, vol. 38.
Beasley, B L, et al., Fenfluramine Hydrochloride Treatment of Parkinsonism, Arch Neurol (Apr. 1977) pp. 255-256, vol. 34.
Beasley, B, Fenfluramine and Parkinson's Disease, Letters to the Editor, Arch Neurol (Nov. 1977) p. 720, vol. 34.
Karoum, F, et al., Metabolism of (-) deprenyl to amphetamine and methamphetamine may be responsible for deprenyl's therapeutic benefit: A biochemical assessment, Neurology (May 1982), pp. 503-509, vol. 32.
Goetz, C G, et al., Bupropion in Parkinson's disease, Neurology (Aug. 1984) pp. 1092-1094, vol. 34.
Wadenberg, M-L, Serotonergic Mechanisms in Neuroleptic-Induced Catalepsy in the Rat, Nueroscience and Biobehavioral Reviews (1996) pp. 325-339, vol. 20:2.
Banjaw, M Y, et al., Anticataleptic Activity of Cathinone and MDMA (Ecstasy) Upon Acute and Subchronic Administration in Rat, Synapse (2003) pp. 232-238, vol. 49.
Sotnikova, T D, et al., Dopamine-Independent Locomotor Actions of Amphetamines in a Novel Acute Mouse Model of Parkinson Disease, PloS Biology (Aug. 2005) pp. 1-13, vol. 3:8 e271.
Request for Applications, Unmet Needs for Treating Symptoms of Parkinson's Disease DOPA Non-Responsive Symptoms of PD, The Michael J. Fox Foundation for Parkinson's Research (Mar. 13, 2006) pp. 1-7.
International Preliminary Report on Patentability, Written Opinion for PCT/US06/29096, Jan. 29, 2008.
Seiden LS et al. Amphetamine: effects on catecholamine systems and behavior. Annu Rev Pharmacol Toxicol. 1993; 32: 639-677.
Sulzer D et al. Amphetamine redistributes dopamine from synaptic vesicles to the cytosol and promotes reverse transport. The Journal of Neuroscience. May 1995; 15(5): 4102-4108.
Fon EA et al. Vesicular transport regulates monoamine storage and release but is not essential for amphetamine action. Neuron. Dec. 1997; 19: 1271-1283.
Jones SR et al. Mechanisms of amphetamine action revealed in mice lacking the dopamine transporter. The Journal of Neuroscience. Mar. 15, 1998; 18(6): 1979-1986.
Amphetamine. Wikipedia. Retrieved Mar. 10, 2011. 17 pp.

* cited by examiner

*Primary Examiner* — Jennifer M Kim
(74) *Attorney, Agent, or Firm* — Myers Bigel Sibley & Sajovec, P.A.

(57) ABSTRACT

A method of treating a subject for Parkinson's disease comprises administering said subject a phenylisopropylamine in an amount effective to treat said Parkinson's disease. In some embodiments the method is used to treat at least a motor symptom of Parkinson's disease; in some embodiments the method is used to treat at least a non-motor symptom of Parkinson's disease.

14 Claims, 11 Drawing Sheets

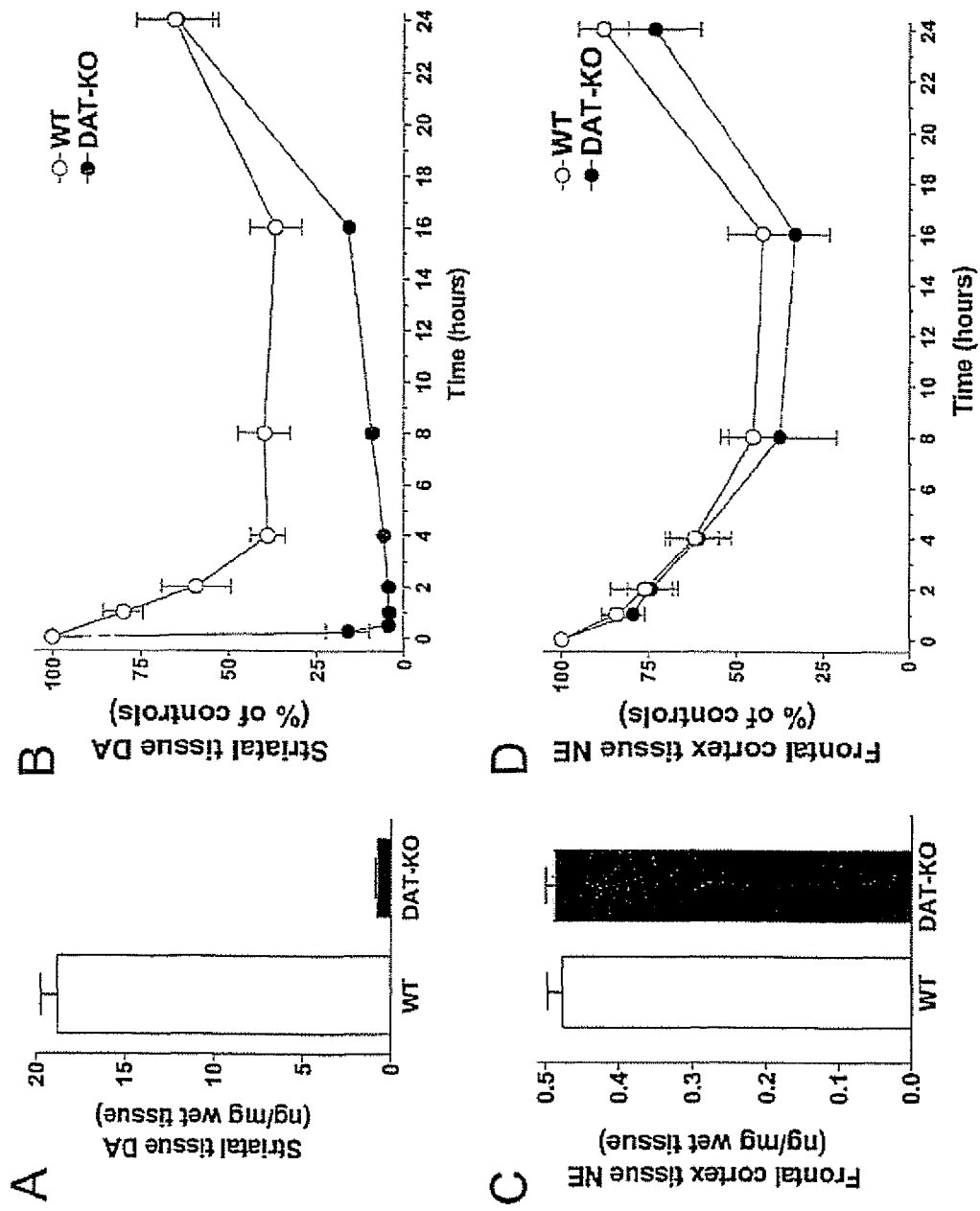
Figure 1 (1 of 2)

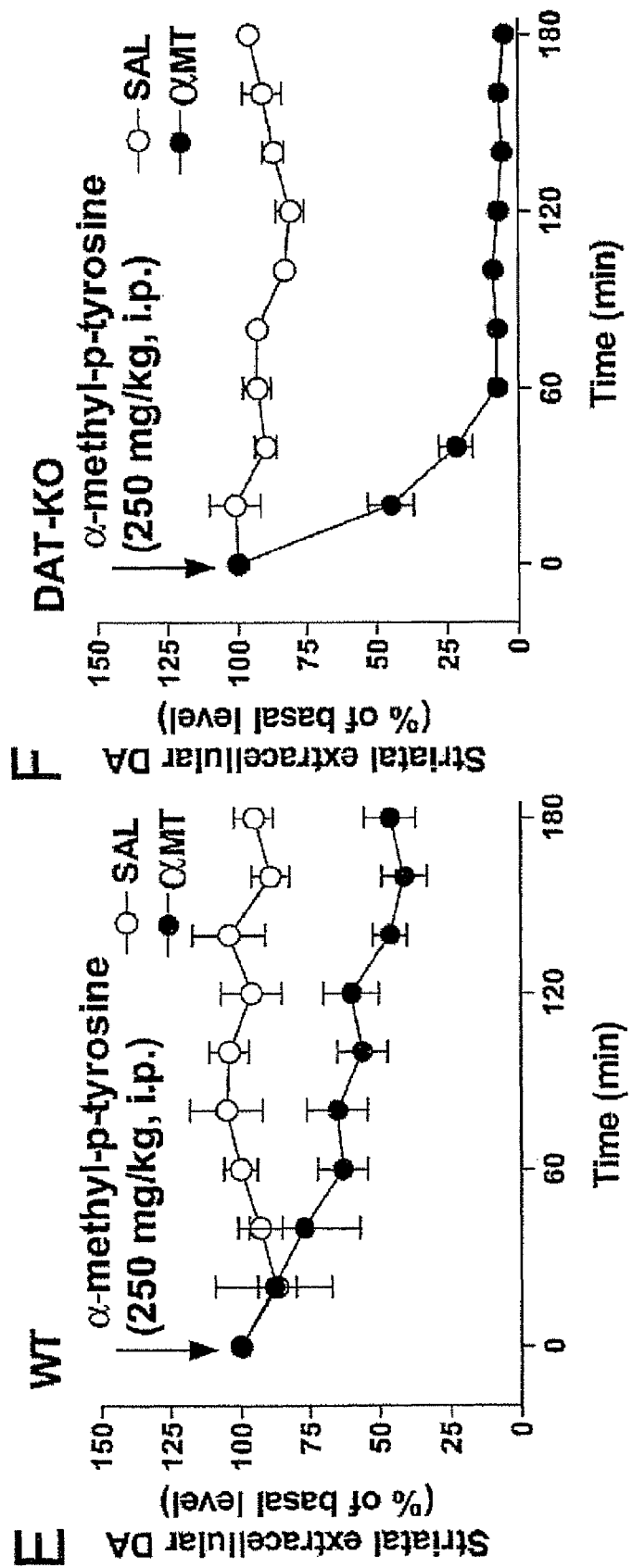
Figure 1 (2 of 2)

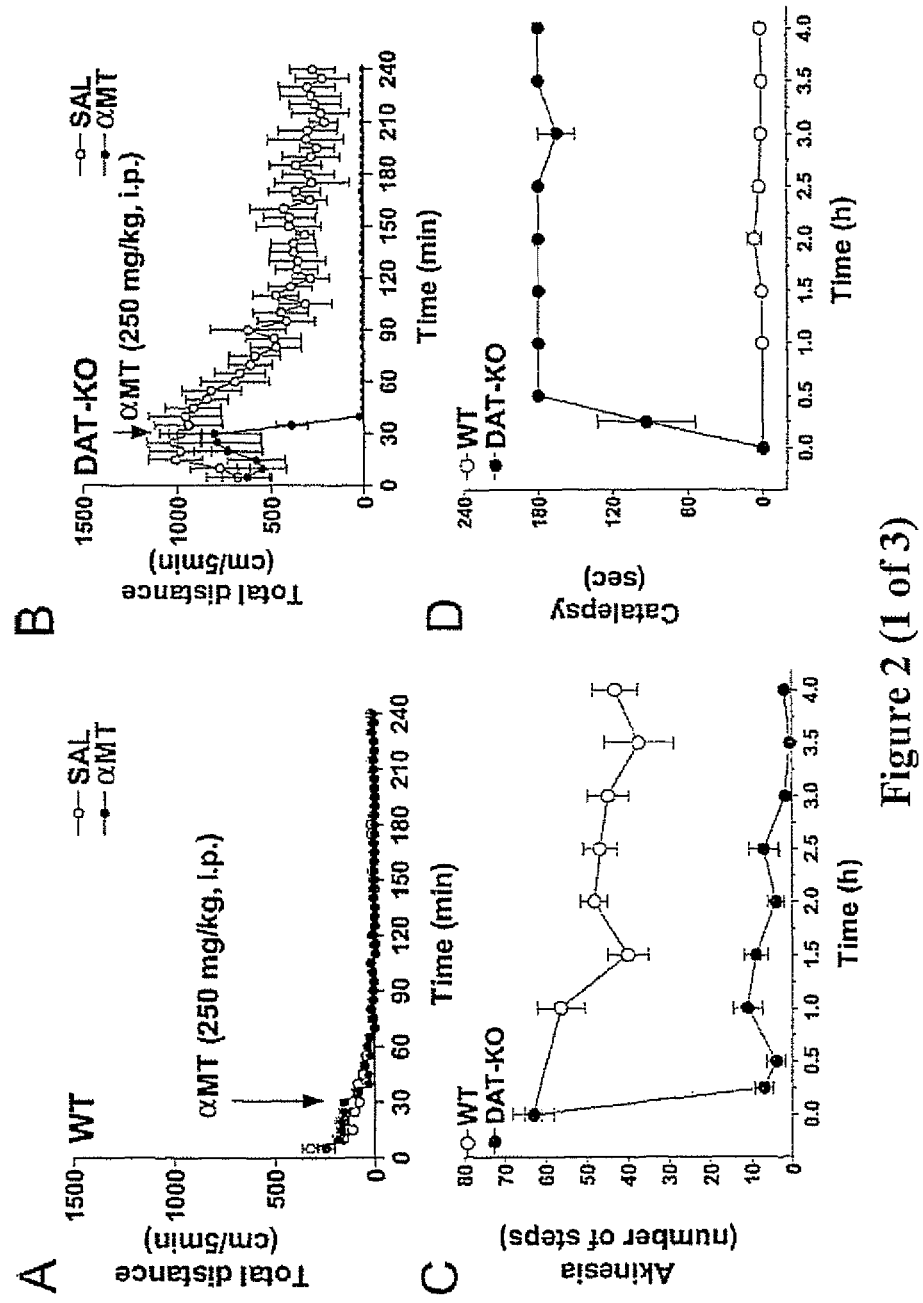
Figure 2 (1 of 3)

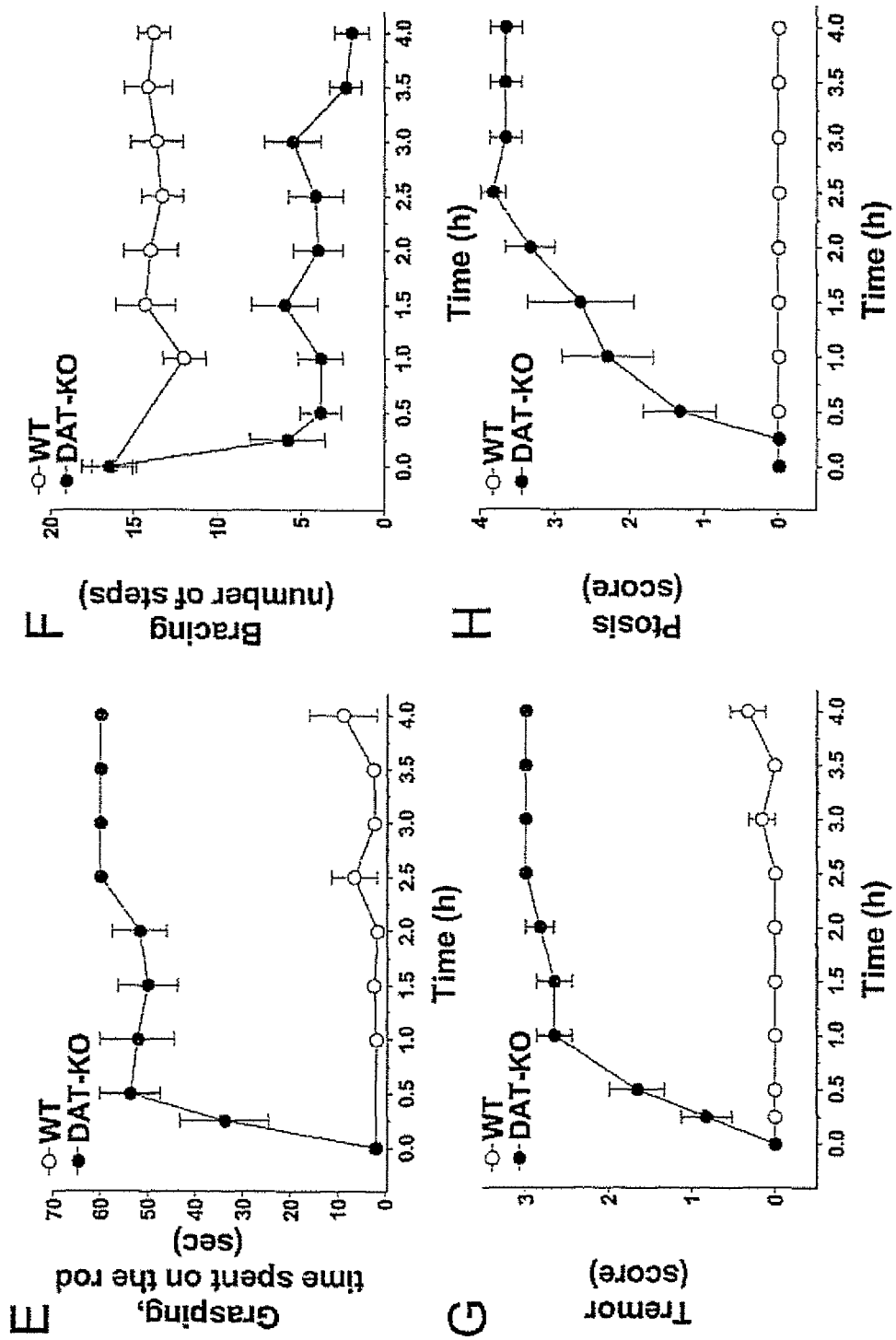
Figure 2 (2 of 3)

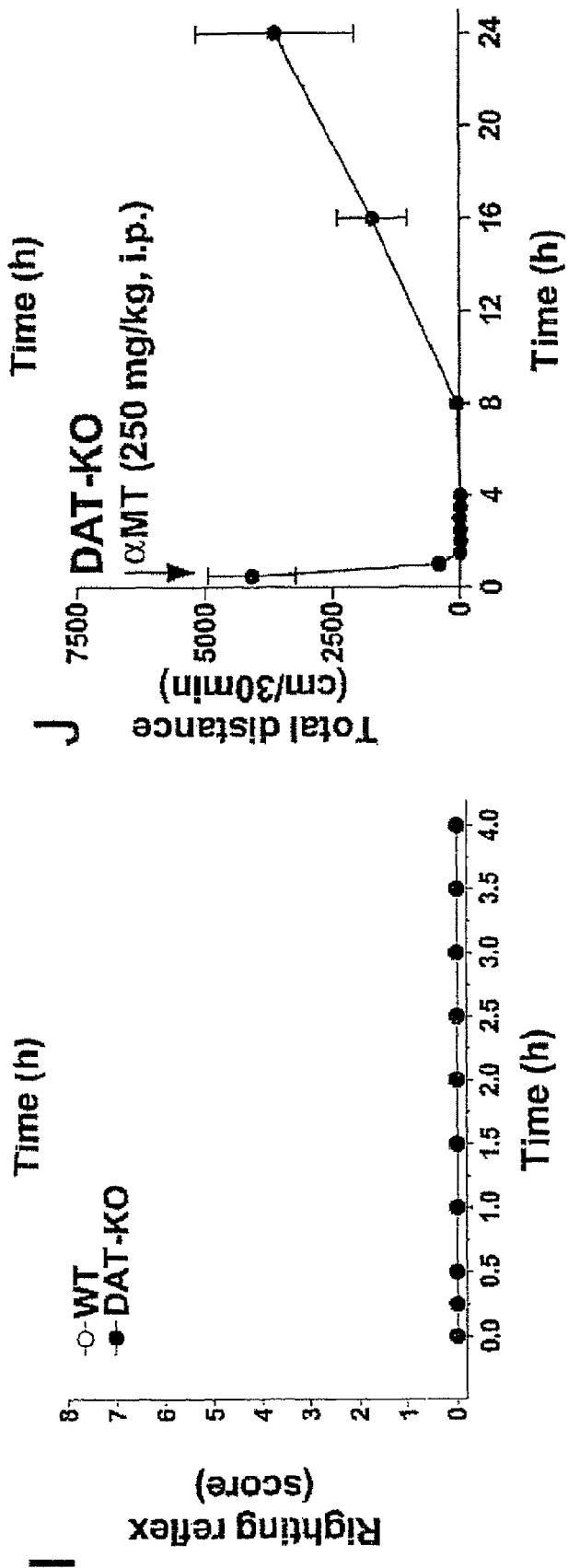
Figure 2 (3 of 3)

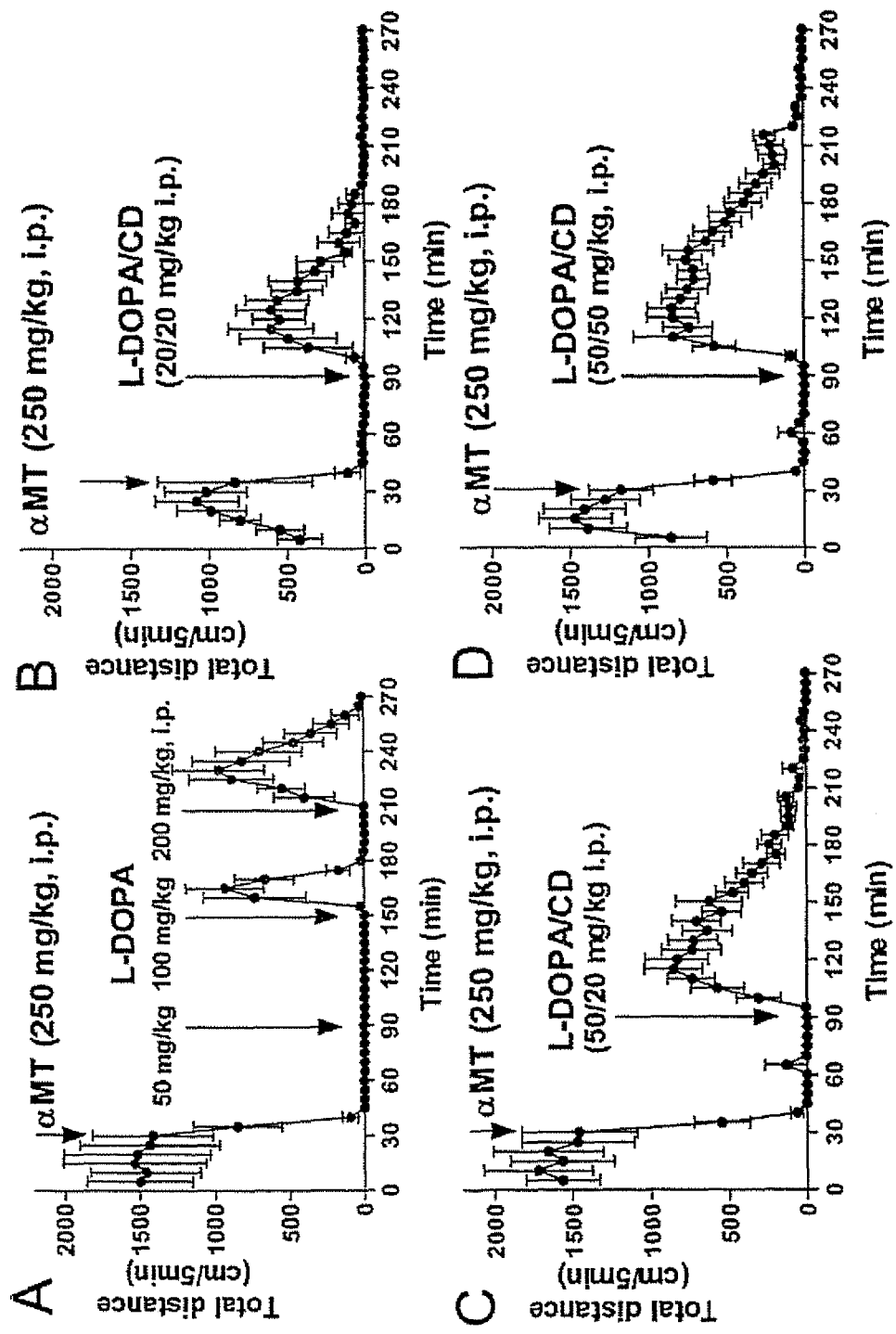
Figure 3 (1 of 3)

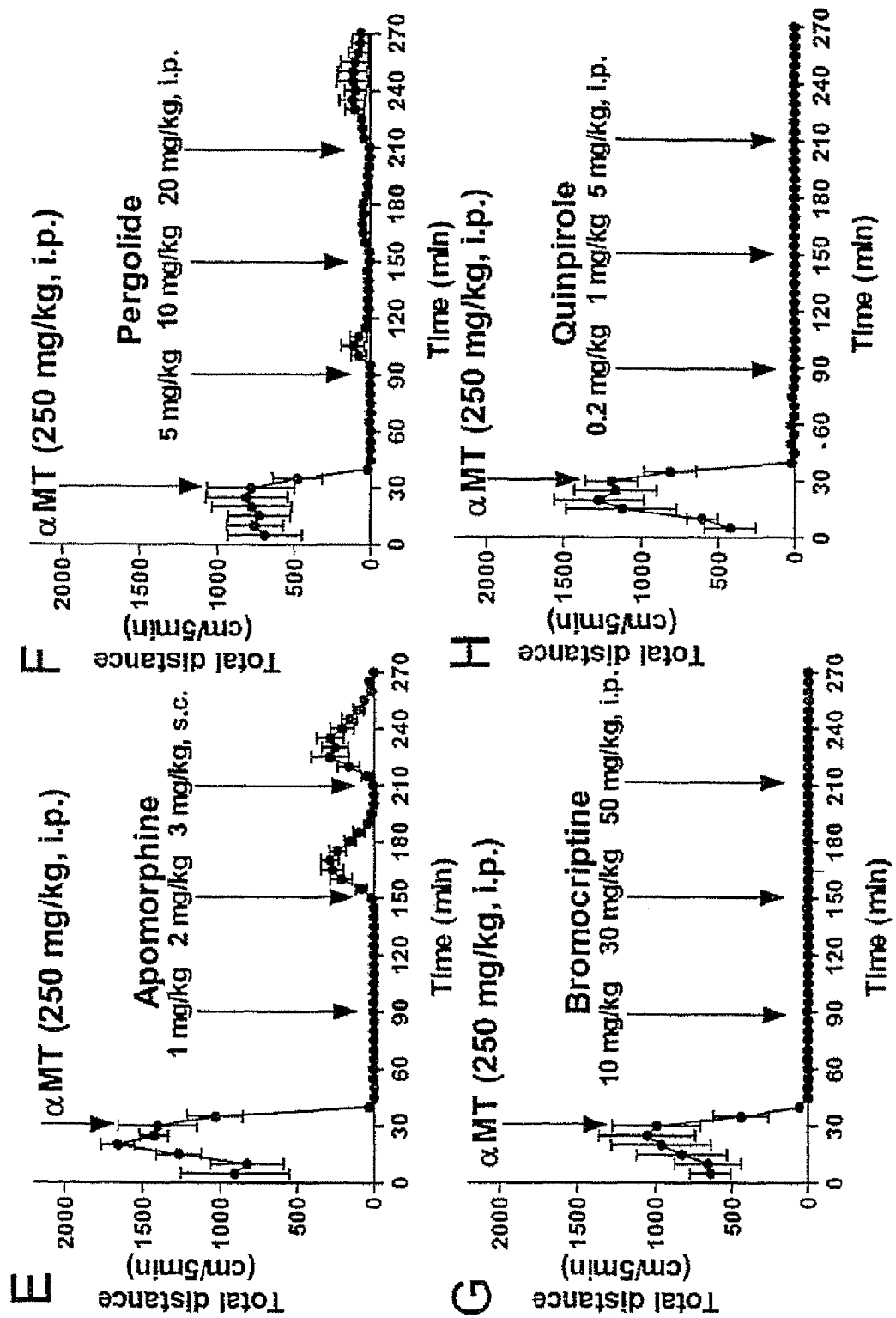
Figure 3 (2 of 3)

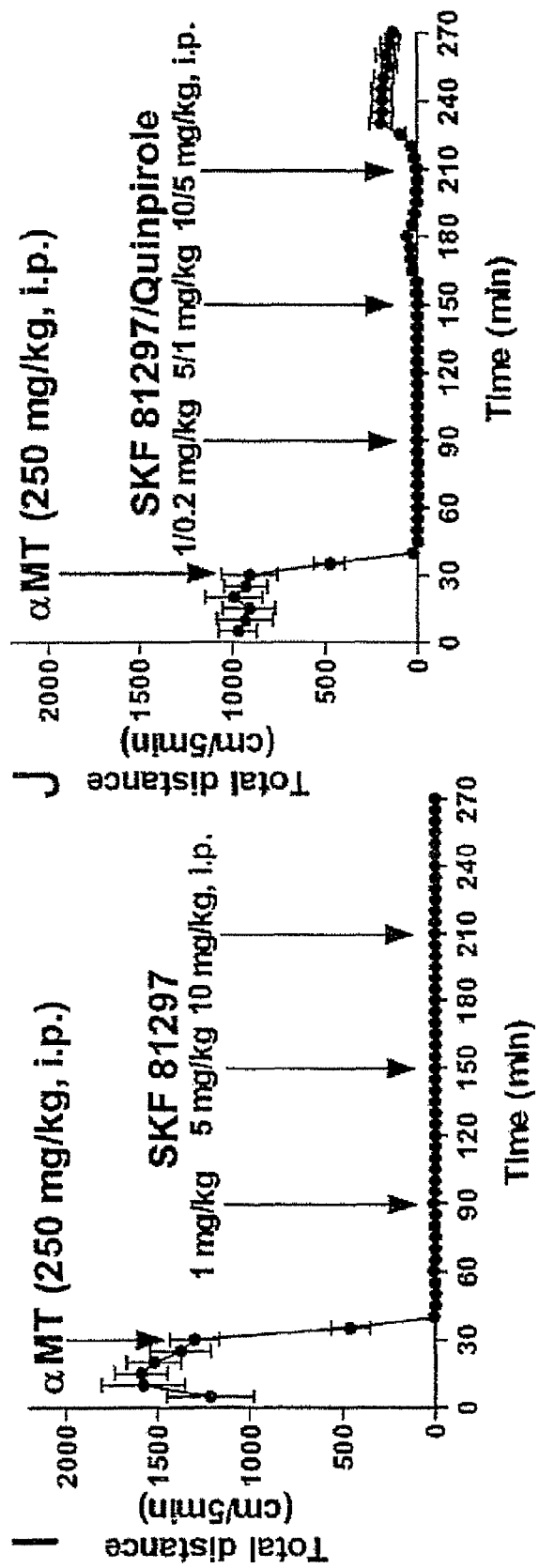
Figure 3 (3 of 3)

ANTIPARKINSONIAN ACTION OF PHENYLISOPROPYLAMINES

RELATED APPLICATIONS

This application claims the benefit of U.S. provisional patent application Ser. No. 60/703,137, filed Jul. 28, 2005, the disclosure of which is incorporated by reference herein in its entirety.

This invention was made with government support under grant nos. NS-19576 and MPH-40159 from the National Institutes of Health. The US Government has certain rights to this invention.

FIELD OF THE INVENTION

The present invention concerns methods of treating Parkinson's disease with phenylisopropylamines.

BACKGROUND OF THE INVENTION

The phenylethylamine derivative dopamine (DA) is critically involved in a wide variety of vital functions such as locomotion, feeding, emotions and reward [1-3]. Major DA systems in the brain originate from brainstem DA neurons located in the substantia nigra pars compacta (SNc) and the ventral tegmental area (VTA). SNc neurons project mainly to the caudate/putamen or dorsal striatum (nigrostriatal system), whereas VTA neurons send their axons to the ventral striatum including the nucleus accumbens, as well as certain other limbic (mesolimbic system) and cortical areas (mesocortical system). Small DA-containing cell groups located primarily in the hypothalamus comprise the tuberoinfundibular DA system [4-6]. DA is synthesized from tyrosine by the rate-limiting enzyme tyrosine hydroxylase (TH), to produce L-DOPA which is quickly decarboxylated by L-aromatic acid decarboxylase (L-AADC) to DA [1,3]. Intraneuronal DA is accumulated into synaptic vesicles by the vesicular monoamine transporter-2 (VMAT2) [7,8]. DA released into the extracellular space exerts its physiological functions via activation of G protein-coupled D1-like and D2-like DA receptors [9]. Finally, DA in the extracellular space is subject to dilution by diffusion and metabolic degradation; however the major route of DA clearance from the extracellular space in the striatum/nucleus accumbens is the rapid recycling of the neurotransmitter back into dopaminergic terminals by the $Na^+/Cl^-$-dependent plasma membrane dopamine transporter (DAT) [10,11]. Recycled DA in the dopaminergic terminals is then stored in the large intracellular storage pool available for subsequent re-release [12,13].

It is well established that DA neurotransmission in both dorsal and ventral striatum is essential for normal locomotor functions, and progressive degeneration of DA neurons in these areas is a known cause of Parkinson's disease (PD). In most cases, PD becomes clinically apparent when the loss of dopaminergic neurons reaches 60%-70%, which leads to functional dysregulation of the related neuronal circuitry [14-17]. Major motor manifestations of DA deficiency in PD include, but are not limited to, resting tremor (tremor occurring in the absence of voluntary movement), rigidity (tonically increased muscle tone), bradykinesia/akinesia (slowness/difficulty in initiating movement), gait disturbance and postural instability, facial masking, and decreased eyeblinking [18].

Presently, there is no known cure for PD [19,20], however its symptoms can be controlled by therapeutic interventions [21]. DA replacement therapy by administration of the DA precursor, L-DOPA, has been used for many years and remains the gold standard for treatment of PD [22,23]. However, the efficacy of this treatment wanes with time, and fluctuations in motor performance as well as psychotic reactions and dyskinesias often develop. DA agonists, as well as several other classes of drugs directly or indirectly affecting DA function (monoamine oxidase [MAO] inhibitors, COMT [catechol-o-methyl transferase] inhibitors, and amantadine), have some beneficial effects in PD patients, but they are mostly used either at early stages of PD or are applied as adjunct medications to enhance the benefits of L-DOPA [21,24,25]. Due to these limitations of existing therapeutic approaches, the development of better anti-Parkinsonian drugs remains a major objective of PD research.

Several lines of evidence suggest that development of novel non-dopaminergic approaches aimed at bypassing impaired dopaminergic transmission would be beneficial in PD, particularly at later stages [16,26-28], however it is still unclear if these treatments would just potentiate action of residual DA or act completely independently of DA. A number of animal models of DA deficiency, based on pharmacologic, neurotoxic, or genetic approaches, have been developed to understand basic pathological processes leading to PD and/or to search for novel principles of therapy [29-36]. However, in rodents, the prolonged absence of DA is not compatible with life [3,7,8], and animals with chronic severe DA depletion are generally not available for routine experimentation.

We have developed mice lacking the functional DAT (DAT-KO mice) [11] that display remarkable alterations in the compartmentalization of DA [12,13,37]. Lack of the DAT-mediated inward transport in these mice results in an elevated extracellular DA and at least 95% decreased intracellular DA stores. Unlike normal animals, these mice demonstrate remarkable dependence of the remaining DA on ongoing synthesis, and pharmacologic blockade of DA synthesis in DAT-KO mice provides an effective approach to eliminate DA acutely [12,13].

Substituted phenylethylamine derivatives, amphetamines, that are structurally similar to DA and the endogenous trace amine beta-phenylethylamine, represent a well-known group of compounds that potently affect psychomotor functions. Amphetamines are known to interact with plasma membrane monoamine transporters, including DAT, norepinephrine (NE) transporter (NET), and serotonin transporter. This complex interaction results in transporter-dependent efflux of monoamines into extracellular space from intraneuronal stores [10,38,39]. It is commonly believed that DAT-mediated efflux of DA is primarily responsible for the psychostimulant and locomotor actions of these drugs [38,40,41]. Intriguingly, recent studies have identified novel transporter-independent targets of amphetamines. It has been shown that amphetamines, as well as β-phenylethylamine, some monoamine metabolites, and several drugs affecting monoaminergic transmission, can directly activate specific G protein-coupled trace amine (trace amine 1 [TA1]) receptors [42] with currently unknown functional consequences [43,44]. Using DA-depleted DAT-KO mice we observed potent DA-independent antiparkinsonian action of several amphetamine derivatives (17 tested phenylisopropylamines were effective as described below).

The following additional references are noted herein:

Parkes J D et al., Amphetamines in the treatment of Parkinson's disease, *J. Neurol Neurosurg Psychiatry* 38(3): 232-7 (1975).

Goetz C G et al., Bupropion in Parkinson's disease, *Neurology* 34(8):1092-4 (1984).

Karoum, F. et al., Metabolism of (-) deprenyl to amphetamine and methamphetamine may be responsible for deprenyl's therapeutic benefit: a biochemical assessment. *Neurology.* 32(5):503-9 (1982).

Schmidt, W. J. et al., Ecstasy counteracts catalepsy in rats, an anti-parkinsonian effect? *Neurosci Lett.* 330(3): 251-4 (2002)

M. L. Wadenberg, Serotonergic mechanisms in neuroleptic-induced catalepsy in the rat. *Neurosci Biobehav. Rev.* 20 325-339 (1996).

Banjaw M Y et al., Anticataleptic activity of cathinone and MDMA (Ecstasy) upon acute and subchronic administration in rat. *Synapse* 49(4):232-8 (2003)

Fuller, R. W., Fenfluramine and Parkinson's disease, *Arch Neurol.* 34(11):720 (1977)

Beasley B L et al., Fenfluramine hydrochloride treatment of parkinsonism, *Arch Neurol.* 34(4):255-6 (1977)(negative study)

Dawirs, R., Use of NeuroactiveSubstances for the Treatment of Parkinson's Disease and Pharmaceutical Combination, US Pat. Application 2004/0147613.

SUMMARY OF THE INVENTION

A first aspect of the present invention is a method of treating a subject for Parkinson's disease, comprising administering said subject an active compound as described herein in an amount effective to treat said Parkinson's disease. In some embodiments, the Parkinson's disease is early onset Parkinson's disease (e.g., the patient is less than 40 years old).

A second aspect of the invention is a method of treating dysphagia in a Parkinson's disease subject, comprising administering said subject an active compound as described herein in an amount effective to treat said dysphagia.

A third aspect of the invention is a method of treating incontinence in a Parkinson's disease subject, comprising administering said subject an active compound as described herein in an amount effective to treat said incontinence.

A further aspect of the invention is a method of treating anxiety in a Parkinson's disease subject, comprising administering said subject an active compound as described herein in an amount effective to treat said anxiety.

A further aspect of the invention is a method of treating depression in a Parkinson's disease subject, comprising administering said subject an active compound as described herein in an amount effective to treat said depression.

A further aspect of the invention is a method of treating sexual dysfunction in a Parkinson's disease subject, comprising administering said subject an active compound as described herein in an amount effective to treat said sexual dysfunction.

A further aspect of the invention is a method of treating fatigue in a Parkinson's disease subject, comprising administering said subject an active compound as described herein in an amount effective to treat said fatigue.

A further aspect of the invention is a method of treating pain associated with Parkinson's disease in a Parkinson's disease subject, comprising administering said subject an active compound as described herein in an amount effective to treat said pain.

A further aspect of the invention is, in a method of treating a subject for Parkinson's disease with an antiparkinson's agent the improvement comprising administering said subject an active compound as described herein in an amount effective to reduce the dosage of said antiparkinson's agent, reduce at least one undesired side effect (such as dyskinesias) of said antiparkinson's agent, and/or synergistically enhance the efficacy of said antiparkinson's agent.

A further aspect of the present invention is a pharmaceutical composition comprising an active agent as described herein in combination with an additional antiparkinson's agent (e.g. levodopa, with or without carbidopa), with the active agent as described herein included in an amount effective to reduce the dosage of said antiparkinson's agent, reduce at least one undesired side effect (such as dyskinesias) of said antiparkinson's agent, and/or synergistically enhance the efficacy of said antiparkinson's agent.

A further aspect of the invention is the use of an active agent as described herein for the preparation of a medicament for carrying out a method as described herein.

BRIEF DESCRIPTION OF THE DRAWINGS

FIG. 1. αMT induces Severe DA Depletion in the Striatum of DAT-KO Mice.

Figure 4:
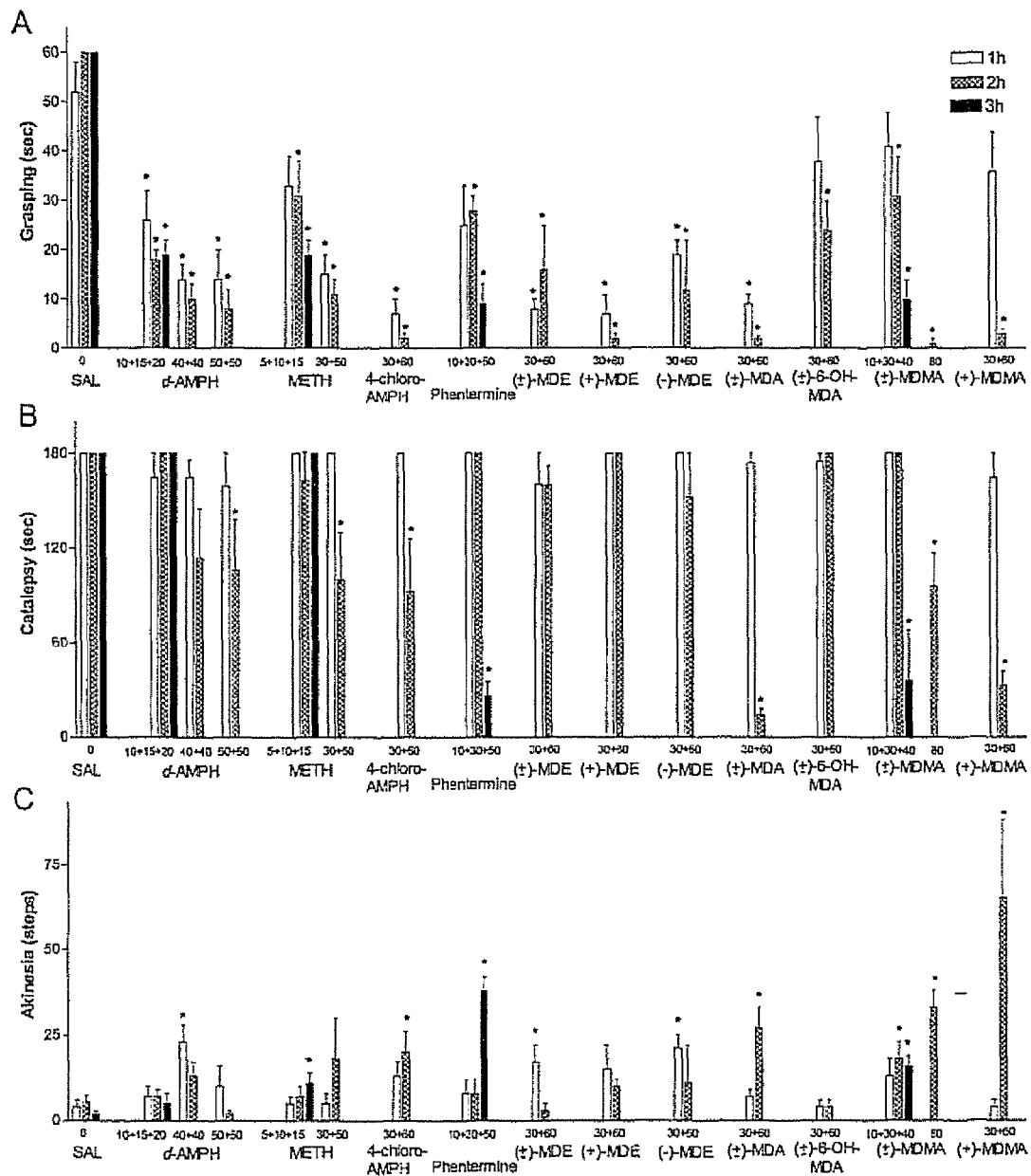

(A) Tissue levels of DA in the striatum of saline-treated control WT and DAT-KO mice (n=7 per group). Striatal levels of DA were significantly lower in DAT-KO versus WT mice ($p<0.05$, Student's t-test).

(B) Dynamics of the effect of αMT (250 mg/kg IP) on striatal tissue DA in WT and DAT-KO mice (n=5-8 per group). DA levels were significantly lower versus control values at all the time points after aMT treatment in DAT-KO mice and 2-24 hours after treatment in WT mice ($p<0.05$, one-way ANOVA followed by Dunnet's multiple comparison test). The magnitude of the effect was significantly different between genotypes from 1 to 16 h after aMT injection ($p<0.05$, two-tailed Mann-Whitney U test).

(C) Tissue levels of NE in the frontal cortex of saline-treated WT and DATKO mice (n=7 per group).

(D) Dynamics of the effect of αMT (250 mg/kg IP) on tissue levels of NE in the frontal cortex of WT and DAT-KO mice (n=5-8 per group). NE levels were significantly lower versus control values at time points 2-16 after αMT treatment in DAT-KO mice and at 4-16 hours after treatment in WT mice ($p<0.05$, one-way ANOVA followed by Dunnet's multiple comparison test). The magnitude of the effect was not different between genotypes at any time point after αMT injection ($p<0.05$, two-tailed Mann-Whitney U test).

(E) Effect of αMT on extracellular DA levels in the striatum of WT mice, measured using in vivo microdialysis. Data are presented as a percentage of the average level of DA measured in at least three samples collected before the drug administration. (Saline, n=5: aMT, n=7). αMT significantly decreased DA levels 60-120 min after treatment ($p<0.05$, two-tailed Mann-Whitney U test versus respective time points in saline-treated controls).

(F) Effect of αMT on extracellular levels of DA in the striatum of DAT-KO mice, measured by using in vivo microdialysis in freely moving mice. Data are presented as a percentage of the average level of DA measured in at least three samples collected before drug administration. (Saline, WT: n=5: DAT-KO: n=4; aMT, WT: n=7; DAT-KO: n=6). αMT significantly decreased DA levels 20-120 min after treatment ($p<0.05$, two-tailed Mann-Whitney U test versus respective time points in saline treated controls). Analysis of area under curve values for 120-min periods after drug administration revealed significant difference between DAT-KO and WT groups ($p<0.05$, two-tailed Mann-Whitney U test). Note also that the basal extracellular levels of DA in DAT-KO mice were significantly higher than in WT mice (predrug concentrations of DA in dialysates were: WT, 76±17 fmol/20 microliters; DAT-KO, 340±63 fmol/20 microliters).

FIG. 2. αMT-Induced Impairment in Motor Control in DAT-KO Mice Dynamics of locomotor activity following systemic administration of OT (250 mg/kg IP) and saline (30 min after placement in the locomotor activity chamber) in WT (A) and DAT-KO (B) mice (n=6-8 per group). Analysis of total distance traveled for 210 min after drug administration revealed significant effect of αMT treatment (p<0.05; Student's t-test) in DAT-KO but not WT mice (WT-saline, 516±50 cm/210 min; WT-αMT, 505±98 cm/210 min; DAT-KO-saline, 18,489±4,795 cm/210 min; DATKO-αMT, 448±75 cm/210 min) αMT (injected at time 0) induced profound alterations in the akinesia (C), catalepsy (D), grasping (E), bracing (F) induced tremor (G), and ptosis (H) tests, but did not affect the righting reflex (1) in DAT-KO mice. Behavioral tests were performed as described in Materials and Methods. At all the time points, DAT-KO mice were significantly different versus respective values (data not shown) of saline-treated DAT-KO controls (p<0.05; Student's t-test n=6 per group) in these tests with exception of 15-min time point for ptosis (H) and all time points for righting reflex test (I). In WT mice only the akinesia test (C) revealed minor, yet significant, effect (1.5-4 h after aMT treatment) versus values (data not shown) of the respective saline treated WT controls (p<0.05; Student's t-test; n=6 per group). No significant alterations in any other test at any time point examined (D-1) was noted in αMT-treated versus saline treated (data not shown) WT mice. Locomotor activity is restored in DAT-KO mice 16-24 h after αMT (250 mg/kg IP) treatment (J).

FIG. 3. L-DOPA and Nonselective DA Agonists Are Effective in Restoring Locomotion in DDD Mice. DAT-KO mice were placed in the locomotor activity chamber and 30 min later were treated with αMT (250 mg/kg IP) and 1 h after αMT were challenged with single or multiple doses of a drug (interval between treatments is 1 h). L-DOPA itself (A) or in combination with carbidopa (B-D) effectively restored locomotion in DDD mice, as revealed by the significant effect of L-DOPA at doses 100 and 200 mg/km IP, or combinations of L-DOPA/carbidopa at closes 20/20, 50/20, and 50/50 mg/kg, IP (analysis of total distance traveled for 1 h after each dose of the drug; p<0.05, two-tailed Mann-Whitney U test versus respective values in saline-treated DDD mice; data not shown). Nonselective DA receptor agonists, apomorphine (E) at doses 2 and 3 mg/kg SC, and pergolide (F) at doses 5, 10, and 20 mg/kg IP, induced locomotion in DDD mice (analysis of total distance traveled for 1 h after each dose of the drug; p<0.05, two-tailed Mann-Whitney U test, versus respective values in saline-treated DDD mice; data not shown). D2 DA receptor agonists bromocriptine (G), quinpirole (H), and D1 DA receptor agonist (+)-SKF 81297 (1) were not effective, but the combinations of D1 and D2 DA agonists (+)-SKF81297 plus quinpirole at doses 5/1 and 10/5 mg/kg IP, induced significant locomotion in DDD mice (analysis of total distance traveled for 1 h after each treatment; p<0.05, two-tailed Mann-Whitney U test versus respective values in saline-treated DDD mice; data not shown). Experiments were performed in 6-12 mice per group.

FIG. 4. Amphetamine Derivatives at High Doses Are Effective in Reversing Abnormal Motor Behaviors of DDD Mice.

DAT-KO mice were placed in the locomotor activity chamber and 30 min later were treated with αMT (250 mg/kg IP), and 1 h after αMT were challenged with single or multiple doses of drugs (in cumulative dosing experiments, the interval between treatments was 1 h). Grasping (A), catalepsy (B), and akinesia (C) tests were performed as described in Materials and Methods 1 h after each dose (the only exception is (+)-MDMA at 80 mg/kg IP where measurements were performed 2 h after the drug administration). An asterisk indicates p<0.05 versus respective values of saline-treated DDD mice (one-way ANOVA followed by Dunnet's multiple comparison test). Experiments were performed in 6-16 mice per group. d-AMPH indicates damphetamine; d-METH, d-methamphetamine; and 4-chloro-AMPH, 4-chloro-amphetamine.

Figure 5:
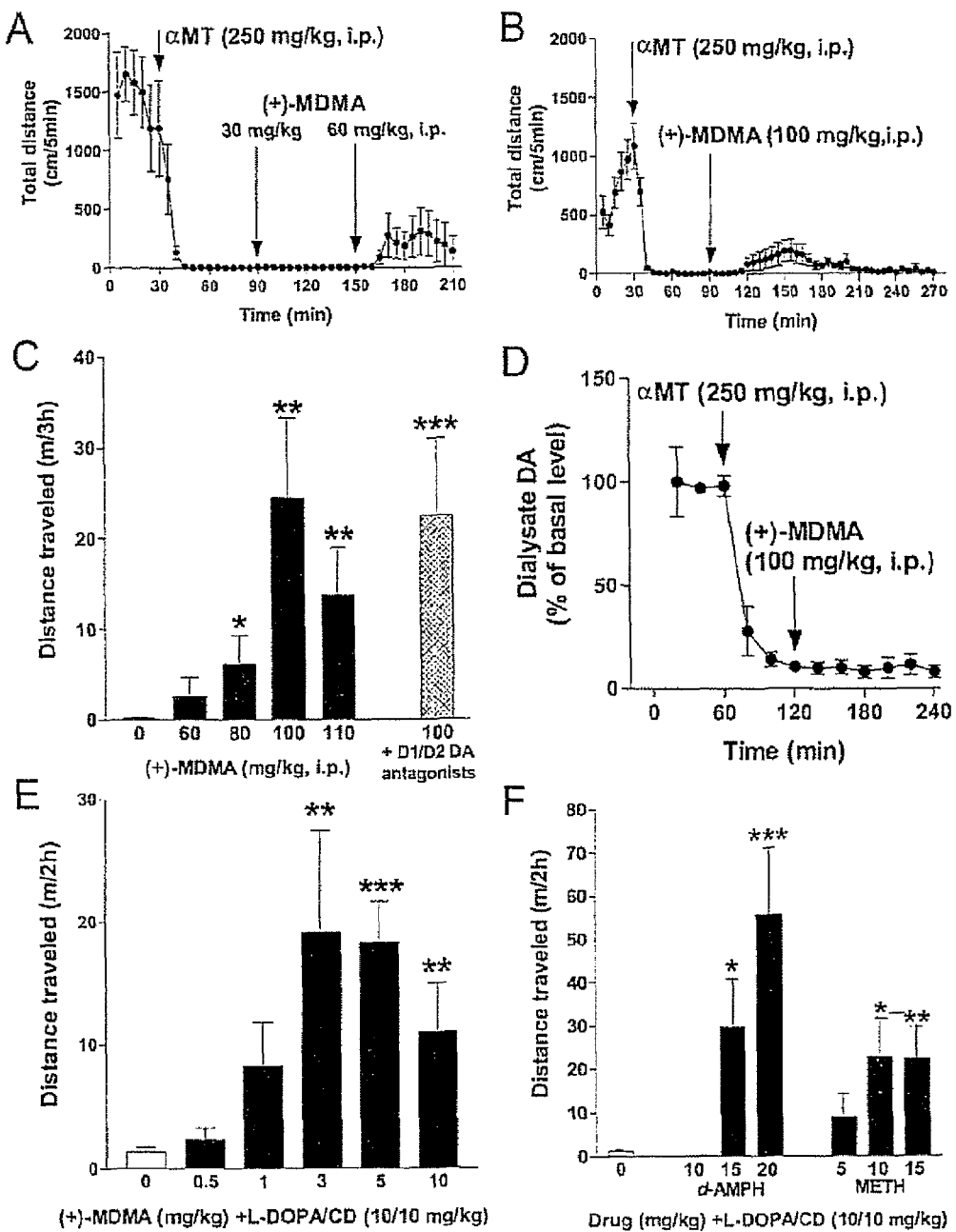

FIG. 5. (+)-MDMA Induces Forward Locomotion in DDU Mice.

(A-C) DAT-KO mice were placed in the locomotor activity chamber and 30 min later were treated with αMT (250) mg/kg IP) and 1 h after αMT were challenged with single (B and C) or multiple doses (A) of a drug (interval between treatments is 1 h) (n ¼ 10-16 per group). Repeated treatment with (+)-MDMA (30 and 60 mg/kg EP) induces forward locomotion in DDD mice (A). Analysis of total distance traveled for 1 h after 60 mg/kg IP of (+)-MDMA reveals significant effect of treatment versus respective period in saline-treated controls (two-tailed Mann-Whitney U test, data not shown). Dynamics (B) and dose-response (C) of locomotor effect of (+)-MDMA in DDD mice are shown. Pretreatment with D1 and D2 DA antagonists (SCH23390, 0.1 mg/kg, SC plus raclopride, 2 mg/kg IP) 30 min before 100 mg/kg IP (+)-MDMA) did not affect locomotor action of (+)-MDMA (C). (D) (+)-MDMA (100 mg/kg IP) fails to affect DA dynamics in the striatum of DDD mice as measured by in vivo microdialysis. Data are presented as a percentage of the average level of DA measured in at least three samples collected before αMT administration (n=4). Analysis of area under curve values for 120-min periods after (+)-MDMA administration revealed no significant difference in comparison with respective values in control group (FIG. 1; p>0.05, two-tailed Mann-Whitney U test). (E and F) (+)-MDMA (E) as well as d-amphetamine and d-methamphetamine (F) at moderate doses potentiate locomotor-stimulating effect of subthreshold dose of L-DOPA/carbidopa (10/10 mg/kg IP). DAT-KO mice were treated with αMT as described above (A-C) and 45 min after αMT were injected with amphetamines. L-DOPA/carbidopa was injected 15 min after amphetamines, and distance traveled for 2 h was measured (n=6-15 per group). Note, that no forward locomotion was observed after these doses of (+)-MDMA, d-amphetamine and d-methamphetamine without L-DOPA/carbidopa, whereas L-DOPA/carbidopa (presented as drug dose 0) induced only a modest but significant (p<0.05) increase in locomotion over saline-treated controls (data not shown). Single asterisk indicates p<0.05; double asterisks indicate p<0.01; and triple asterisks indicate p<0.001 versus saline-treated controls (C) or L-DOPA/carbidopa-treated (10/10 mg/kg IP) group (E and F) (two-tailed Mann-Whitney U test). d-AMPH, d-amphetamine; METH, methamphetamine.

Figure 6:
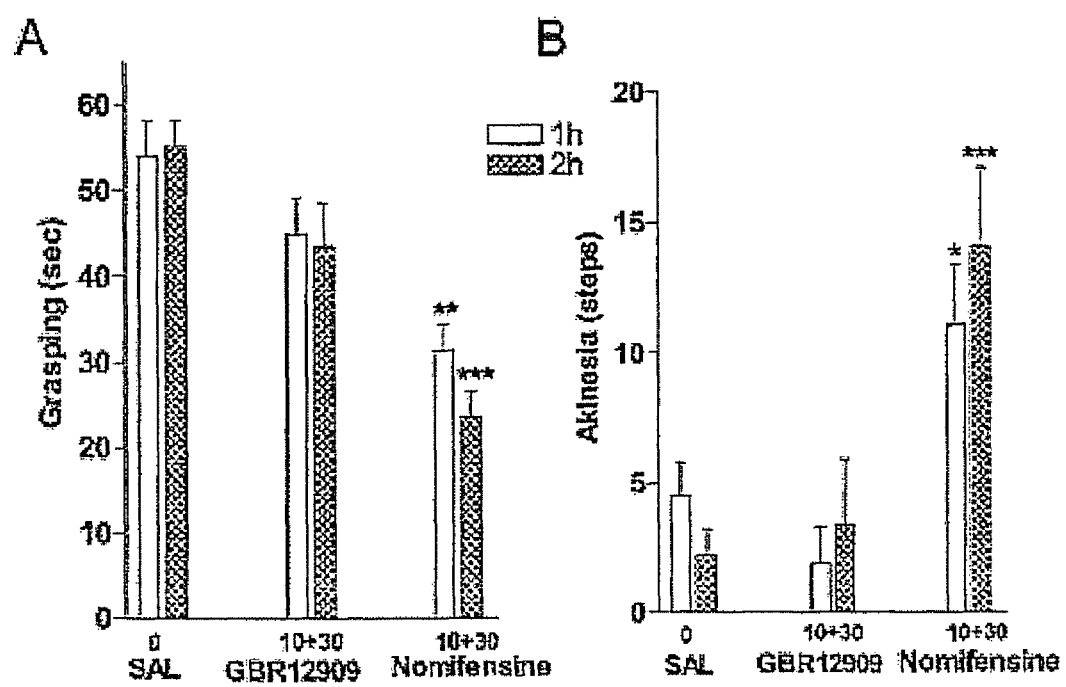

FIG. 6. Nomifensine, but not GBR12909, is effective in reversing abnormal motor behaviors of DDD mice. DAT-KO mice were placed in the locomotor activity chamber and 30 min later were treated with αMT (250 mg/kg IP). Mice were challenged 1 h later with two doses (10 and 30 mg/kg IP) of each drug or saline with a 1 h interval between treatments (n=9-15 per group). Grasping (A) and akinesia (B) tests were performed as described in Materials and Methods 1 h after each dose. A single asterisk indicates p<0.05, double asterisks indicate p<0.01, and triple asterisks indicate p<0.001 versus respective values of saline-treated DDD mice (one-way ANOVA followed by Dunnet's multiple comparison test), Note that no significant differences between GBR12909-treated mice and saline-treated controls in both tests were found, whereas nomifensine-treated mice were significantly different frown GBR12909-treated mice (p<0.05) in both experimental paradigms and doses tested.

DETAILED DESCRIPTION OF PREFERRED EMBODIMENTS

"Antiparkinson's agent" as used herein includes, but is not limited to: levodopa (L-DOPA; with or without carbidopa), dopamine agonists (such as apomorphine, bromocriptine, pergolide, pramipexole, ropinirole, etc.) anticholinergics such as atropine, scopolamine, glycopyrrolate, trihexyphenidyl, benztropine mesylate, procyclidine, etc.), monoamine oxidase (MAO-B) inhibitors such as selegiline, COMT inhibitors (preferably taken with levodopa) such as entacapone and tolcapone and other medications such as amantadine, etc., and including pharmaceutically acceptable salts and prodrugs thereof, and combinations of any of the foregoing. See, e.g., U.S. Pat. No. 6,833,478.

"Parkinson disease" or "Parkinson's disease" as used has its conventional meaning and generally refers to a disease characterized by the chronic, progressive loss of neurons in the re-ion of the brain known as the substantia nigra, at any point. Parkinson's disease (including early onset and late onset Parkinson's disease) is characterized by both motor symptoms and non-motor symptoms. In some embodiments of the present invention subjects are early stage Parkinson disease subjects (e.g., subjects in stages I or II of the Hoehn and Yahr Staging scale, or subjects with a score less than 120 or 100 on the Unified Parkinson Disease Rating Scale (UPDRS); in some embodiments of the present invention subjects are late stage Parkinson disease subjects (e.g., subjects in stages 1V or V of the Hoehn and Yahr Staging scale, and or subjects with a score greater than 100 or 120 on the UPDRS) (including late stage early onset Parkinson's disease and late stage late onset Parkinson's disease). In some embodiments the patients to be treated have acquired tolerance to, or have acquired undesired side effects in response to, other antiparkinson's agents such as L-DOPA.

"Motor symptom" of Parkinson's disease as used herein refers to symptoms such as tremor, rigidity, difficulty of maintaining balance or gait, and/or general slowness of movement (also called "bradykinesia"). In some embodiments the active compounds of the present invention are administered in an amount effective to treat motor symptoms (at least one motor symptom) of Parkinson's disease.

"Non-motor symptom" of Parkinson's disease as used herein refers to one or more symptoms such as cognitive dysfunction, autonomic dysfunction, sleep disorders, neurobehavioral abnormalities, depression, constipation, pain, fatigue, etc. In some embodiments the active compounds of the present invention are administered in an amount effective to treat non-motor symptoms (at least one non-motor symptom) of Parkinson's disease.

"Levodopa nonresponsive subject" as used herein refers to a Parkinson's disease patient who has one or more symptom (e.g., a motor symptom) that is no longer effectively managed by dopamine replacement therapy (levodopa administration, with or without carbidopa and/or a COMT inhibitor).

The term "treat" as used herein refers to any type of treatment that imparts a benefit to a patient afflicted with a disease, including improvement in the condition of the patient (e.g., in one or more symptoms), delay in the progression of the disease, reduction of tolerance or increase in efficacy of another antiparkinson's agent, reduction in dose and corresponding reduction in undesired side effects of another antiparkinson's agent, etc.

The term "pharmaceutically acceptable" as used herein means that the compound or composition is suitable for administration to a subject to achieve the treatments described herein, without unduly deleterious side effects in light of the severity of the disease and necessity of the treatment.

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

The present invention is primarily concerned with the treatment of human subjects, but the invention may also be carried out on animal subjects, particularly mammalian subjects such as mice, rats, dogs, cats, livestock and horses for veterinary purposes, and for drug, screening and drug development purposes.

"Alkyl," as used herein, refers to a straight or branched chain hydrocarbon containing from 1 to 10 carbon atoms, or 1 to 4 carbon atoms for loweralkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Halo" as used herein refers to —Cl, —Br, —I or —F.

"Haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Haloalkoxy," as used herein, refers to an alkoxy group, as defined herein, having at least one halo group (e.g. one, two, three) substituted thereon. Representative examples of haloalkoxy include, but are not limited to, trifluoromethyl, 2-chloroethoxy, difluoromethoxy, 1,2-difluoroethoxy, 2,2,2-trifluoroethoxy, trifluoromethoxy, and the like.

"Haloalkthio," as used herein, refers to an alkthio group, as defined herein, having at least one halo group (e.g., one, two, three) substituted thereon.

"Hydroxy," as used herein, refers to an —OH group.

"Nitro," as used herein, refers to a —$NO_2$ group.

"Oxo," as used herein, refers to a =O moiety.

The disclosures of all US Patent references cited herein are to be incorporated by reference herein in their entirety.

1. Active Compounds.

Active compounds of the present invention include phenylisopropylamines. Such compounds are known and described in, for example, Alexander T. Shulgin, Psychotomimetic Drugs: Structure-Activity Relationships, Chapter 6 in *Handbook of Psychopharmacology*, Volume 11: Stimulants (Edited by Leslie L. Iversen Susan D. Iversen and Solomon H. Snyder), Plenum Press, New York 1978).

In some embodiments the active compounds are those described in U.S. Pat. No. 3,547,999.

In some embodiments active compounds useful for carrying out the present invention include compounds of Formula I:

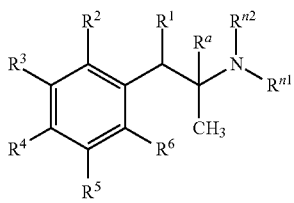

(I)

wherein:

$R^{n1}$, $R^{n2}$ and $R^a$ are each independently selected from the group consisting of H, hydroxy, and loweralkyl;

$R^1$ is selected from the group consisting of H, hydroxy and oxo (=O); and $R^2$, $R^3$, $R^4$, $R^5$ and $R^6$ are each independently selected from the group consisting of H, halo, loweralkyl, haloalkyl, loweralkoxy, haloloweralkoxy; loweralkylthio, haloloweralkylthio, and nitro;

or an adjacent pair of $R^2$ and $R^3$, $R^1$ and $R^4$, or $R^4$ and $R^5$ may together form a group of the formula —OCH$_2$O—;

or a pharmaceutically acceptable salt or prodrug thereof.

(a) In some embodiments, active compounds of the present invention are preferably compounds of Formula Ia:

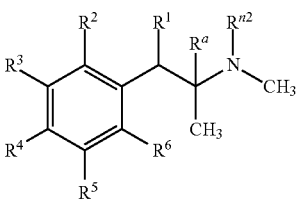

(Ia)

wherein:

$R^{n2}$ and $R^a$ are each independently selected from the group consisting of H, hydroxy, and loweralkyl;

$R^1$ is selected from the group consisting of H, hydroxy and oxo (=O); and $R^2$, $R^3$, $R^4$, $R^5$ and $R^6$ are each independently selected from the group consisting of H, halo, loweralkyl, haloalkyl, loweralkoxy, haloloweralkoxy; loweralkylthio, haloloweralkylthio, and nitro;

or an adjacent pair of $R^2$ and $R^3$, $R^3$ and $R^4$, or $R^4$ and $R^5$ may together form a group of the formula —OCH$_2$O—;

or a pharmaceutically acceptable salt or prodrug thereof.

(b) In some embodiments, active compounds of the present invention are preferably compounds of Formula Ib:

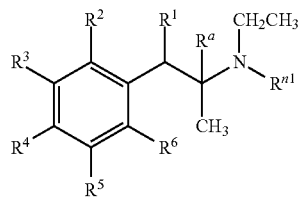

(Ib)

wherein:

$R^{n2}$ and $R^a$ are each independently selected from the group consisting of H, hydroxy, and loweralkyl;

$R^1$ is selected from the group consisting of H, hydroxy and oxo (=O); and $R^2$, $R^3$, $R^4$, $R^5$ and $R^6$ are each independently selected from the group consisting of H, halo, loweralkyl, haloalkyl, loweralkoxy, haloloweralkoxy; loweralkylthio, haloloweralkylthio, and nitro;

or an adjacent pair of $R^2$ and $R^3$, $R^3$ and $R^4$, or $R^4$ and $R^5$ may together form a group of the formula —OCH$_2$O—;

or a pharmaceutically acceptable salt or prodrug thereof.

(c) In some embodiments, active compounds of the present invention are preferably compounds of Formula Ic:

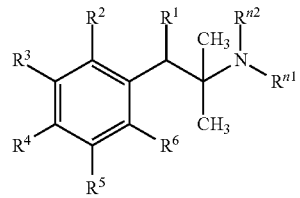

(Ic)

wherein:

$R^{n1}$ and $R^{n2}$ are each independently selected from the group consisting of H, hydroxy, and loweralkyl;

$R^1$ is selected from the group consisting of H, hydroxy and oxo (=O); and $R^2$, $R^3$, $R^4$, $R^5$ and $R^6$ are each independently selected from the group consisting of H, halo, loweralkyl, haloalkyl, loweralkoxy, haloloweralkoxy; loweralkylthio, haloloweralkylthio, and nitro;

or an adjacent pair of $R^2$ and $R^3$, $R^3$ and $R^4$, or $R^4$ and $R^5$ may together form a group of the formula —OCH$_2$O—;

or a pharmaceutically acceptable salt or prodrug thereof.

(d) In some embodiments, active compounds of the present invention are preferably compounds of Formula I, subject to the proviso that at least one of $R^2$, $R^3$, $R^4$, $R^5$ and $R^6$ is halo.

The active compounds including compounds of Formula I contain an asymmetric carbon atom and thus normally occur as a racemic mixture of the dextro- and levorotatory optical isomers. Both dextro- and levorotatory isomers of these compounds, as well as the racemic mixtures, are useful in the compositions and methods described herein.

Specific examples of active compounds useful for carrying out at least some embodiments of the present invention include, but are not limited to:

(1) Methoxylated Phenylisopropylamines, such as:
4-Methoxyphenylisopropylamine;
3,4-Dimethoxyphenylisopropylamine;
2,4-Dimethoxyphenylisopropylamine;
2,5-Dimethoxyphenylisopropylamine;
3,4,5-Trimethoxyphenylisopropylamine;

2,4,5-Trimethoxyphenylisopropylamine;
2,3,4-Trimethoxyphenylisopropylamine;
2,3,5-Trimethoxyphenylisopropylamine;
2,3,6-Trimethoxyphenylisopropylamine;
2,4,6-Trimethoxyphenylisopropylamine; and
2,3,4,5-Tetramethoxyphenylisopropylamine;
(2) Methylenedioxyphenylisopropylamines, such as:
3,4-Methylenedioxyphenylisopropylamine;
N-Methyl-3,4-methylenedioxyphenylisopropylamine;
N-Ethyl-3,4-methylenedioxyphenylisopropylamine;
3-Methoxy-4,5-methylenedioxyphenylisopropylamine;
3-Methoxy-4,5-ethylenedioxyphenylisopropylamine;
2-Methoxy-4,5-methylenedioxyphenylisopropylamine;
2-Methoxy-3,4-methylenedioxyphenylisopropylamine;
4-Methoxy-2,3-methylenedioxyphenylisopropylamine;
6-Methoxy-2,3-methylenedioxy-phenylisopropylamine;
6-methoxy-2,3-methylenedioxyphenylisopropylamine; and
2,3-Dimethoxy-4,5-methylenedioxyphenylisopropylamine;
(3) Alkoxyphenylisopropylamines, such as:
4-Benzyloxy-3,5-dimethoxyphenylisopropylamine;
4-Ethoxy-2,5-dimethoxyphenylisopropylamine;
2-Ethoxy-4,5-dimethoxyphenylisopropylamine;
5-Ethoxy-2,4-dimethoxyphenylisopropylamine; and
4-(n)-Propoxy-2,5-dimethoxyphenylisopropylamine;
(4) Alkylphenylisopropylamines, such as:
4-Methylphenylisopropylamine;
2-Methylphenylisopropylamine;
3-Methylphenylisopropylamine;
3,4-Dimethylphenylisopropylamine;
2,5-Dimethylphenylisopropylamine;
2,5-Dimethoxy-4-methylphenylisopropylamine;
2,6-Dimethoxy-4-methylisopropylamine;
2,5-Dimethoxy-4-ethylphenylisopropylamine;
2,5-Dimethoxy-4-propylphenylisopropylamine;
2,5-Dimethoxy-4-butylphenylisopropylamine;
2,5-Dimethoxy-4-amylphenylisopropylamine; and
6-(2-Aminopropyl)-2,2-dimethyl-5-methoxy-2,3-dihydrofuran;
(5) Halo- or Sulfur-Substituted Phenylisopropylamines, such as:
4-Chlorophenylisopropylamine;
4-Chloro-N-methylphenylisopropylamine;
4-Bromo-N-methylphenylisopropylamine;
4-Bromo-2,5-dimethoxyphenylisopropylamine;
2-Bromo-4,5-methylenedioxyphenylisopropylamine; and:
4-Bromo-3,5-dimethoxyphenylisopropylamine; and:
(6) Brominated Alkoxylated Phenylisopropylamines;
4-Iodo-2,5-dimethoxyphenylisopropylamine;
4-Thiomethyl-2,5-dimethoxyphenylisopropylamine; and
4-Thioethyl-2,5-dimethoxyphenylisopropylamine.
Additional examples of active compounds useful for carrying out at least some embodiments of the present invention include but are not limited to the following
4-Methylthio-2,5-dimethoxyamphetamine;
4-Ethylthio-2,5-dimethoxyamphetamine;
4-Isopropylthio-2,5-dimethoxyamphetamine;
4-Phenylthio-2,5-dimethoxyamphetamine;
4-Propylthio-2,5-dimethoxyamphetamine;
4-allyloxy-3,5-dimethoxyamphetamine;
2,5-dimethoxy-4-(beta-methallylthio)amphetamine;
2,5-dimethoxy-4-allylthioamphetamine;
2,5-dimethoxy-4-cyclohexylthioamphetamine;
2,5-dimethoxy-4-(2-fluoroethylthio)amphetamine;
3,5-dimethoxy-4-bromoamphetamine;
2,5-Bismethylthio-4-methylamphetamine;
2,5-Dimethoxy-4,N-dimethylamphetamine;
N-cyclopropyl-2,5-dimethoxy-4-methylamphetamine;
4-Bromo-3,5-dimethoxyamphetamine;
2-Bromo-4,5-methylenedioxyamphetamine;
4-Benzyloxy-3,5-dimethoxyamphetamine;
4-Ethoxy-3,5-dimethoxyamphetamine;
2,4-Dimethoxyamphetamine;
3,4,5-trimethylamphetamine;
2,4-dimethoxy-N,N-dimethylamphetamine;
2,4-dimethoxy-N,N-dimethyl-5-iodoamphetamine;
2,4-dimethoxy-N,N-dimethyl-5-fluoroamphetamine;
N,N-diethyl-2,4-dimethoxyamphetamine;
N,N-dimethyl-2-ethoxy-4-methoxyamphetamine;
2-(n)-butyloxy-N,N-dimethyl-4-methoxy-amphetamine;
2-(n)-decyloxy-N,N-dimethylamphetamine;
2,4-diethoxy-N,N-dimethylamphetamine;
N,N-dimethyl-2,4-di-(i)-propoxyamphetamine;
5-bromo-2,4-dimethoxyamphetamine;
2,5-Dimethoxyamphetamine;
3,4-dimethylamphetamine;
2,5-dimethoxy-N,N-dimethylamphetamine;
4-fluoro-2,5-dimethoxy-N,N-dimethylamphetamine;
2,5,N,N-tetramethylamphetamine;
3,4-Dimethoxyamphetamine;
3-bromo-2,6-dimethoxy-N,N-dimethylamphetamine
3-iodo-2,6-dimethoxy-N,N-dimethylamphetamine
3,5-dimethoxy-N,N-dimethylamphetamine
2,5-Dimethoxy-3,4-methylenedioxyamphetamine;
2,5-dimethoxy-N-methyl-3,4-methylenedioxyamphetamine;
2,3-Dimethoxy-4,5-methylenedioxyamphetamine;
4-Amyl-2,5-dimethoxyamphetamine;
4-Bromo-2,5-dimethoxyamphetamine;
4-Butyl-2,5-dimethoxyamphetamine;
2,5-dimethoxy-4-(2-methylpropyl)-amphetamine;
2,5-dimethoxy-4-(1-methylpropyl)amphetamine;
2,5-dimethoxy-4-(1,1-dimethylethyl)amphetamine;
2,5-dimethoxy-4-cyclo-propylmethylamphetamine;
4-Chloro-2,5-dimethoxyamphetamine;
2,5-dimethoxy-4-acetamidoamphetamine;
4-(2-Fluoroethyl)-2,5-dimethoxyamphetamine;
4-Ethyl-2,5-dimethoxyamphetamine;
4-Iodo-2,5-dimethoxyamphetamine;
4-Methyl-2,5-dimethoxyamphetamine;
2,4-dimethoxy-5-methylamphetamine;
4,5-dimethoxy-2-methylamphetamine;
4-Methyl-2,6-dimethoxyamphetamine;
4-Nitro-2,5-dimethoxyamphetamine;
4-Propyl-2,5-dimethoxyamphetamine;
2,5-dimethoxy-4-(1-hydroxypropyl)-amphetamine;
2,5-dimethoxy-4-ethoxyamphetamine;
3,5-dimethoxy-4-ethoxyamphetamine;
2,4,5-Triethoxyamphetamine;
2,4-Diethoxy-5-methoxyamphetamine;
2,5-Diethoxy-4-methoxyamphetamine;
2-Ethoxy-4,5-dimethoxyamphetamine;
Benzofuran-2-methyl-5-methoxy-6-(2-aminopropane);
6-(2-aminopropyl)-5-methoxy-2-methyl-2,3-dihydrobenzofuran;
7-(2-aminopropyl)-5-methoxy-2-methyl-2,3-dihydrobenzofuran;
Benzofuran-2,2-dimethyl-5-methoxy-6-(2-aminopropane);
6-(2-aminopropyl)-2,2-dimethyl-5-methoxy-2,3-dihydrobenzofuran;
7-(2-aminopropyl)-2,2-dimethyl-5-methoxy-2,3-dihydrobenzofuran;
6-(2-aminopropyl)-5-methoxy-2,3,3-trimethyl-2,3-dihydrobenzofuran;

6-(2-aminopropyl)-2,3-dimethyl-5-methoxy-2,3-dihydrobenzofuran;
6-(2-aminopropyl)-2-ethyl-5-methoxy-2,3-dihydrobenzofuran;
7-(2-aminopropyl) 6-methoxy-1,2,3,4-tetrahydrobenzopyran;
N-Hydroxy-N-methyl-3,4-methylenedioxyamphetamine;
3,4-Trimethylene-2,5-dimethoxyamphetamine;
3,4-Tetramethylene-2,5-dimethoxyamphetamine;
3,4-Norbornyl-2,5-dimethoxyamphetamine;
3,4-Dimethyl-2,5-dimethoxyamphetamine;
1,4-Dimethoxynaphthyl-2-isopropylamine;
2,5-Dimethoxy-N,N-dimethyl-4-iodoamphetamine;
5-Ethoxy-2-methoxy-4-methylamphetamine;
4-Methoxyamphetamine;
2,N-Dimethyl-4,5-methylenedioxyamphetamine;
2,N-dimethyl-3,4-methylenedioxyamphetamine;
3,4-Methylenedioxyamphetamine;
2,3-methylenedioxyamphetamine;
N-Allyl-3,4-methylenedioxyamphetamine;
N-Butyl-3,4-methylenedioxyamphetamine;
N-butylamphetamine;
N-ethylamphetamine;
N-methylamphetamine;
N-Benzyl-3,4-methylenedioxyamphetamine;
3,4-methylenedioxy-N-(i)-butylamphetamine;
3,4-methylenedioxy-N-(t)-butylamphetamine;
3,4-methylenedioxy-N-amylamphetamine;
3,4-methylenedioxy-N-(n)-hexylamphetamine;
3,4-methylenedioxy-N-(4-heptyl)-amphetamine;
3,4-methylenedioxy-N-(n)-octylamphetamine;
3,4-methylenedioxy-N,N-diethylamphetamine;
3,4-methylenedioxy-N-(t)-butylaminoamphetamine;
N-Cyclopropylmethyl-3,4-methylenedioxyamphetamine;
N,N-Dimethyl-3,4-methylenedioxyamphetamine;
N-Ethyl-3,4-methylenedioxyamphetamine;
N-(2-Hydroxyethyl)-3,4-methylenedioxyamphetamine;
N-Isopropyl-3,4-methylenedioxyamphetamine;
N-Methyl-3,4-methylenedioxyamphetamine;
N-Methyl-3,4-ethylenedioxyamphetamine;
N-Methoxy-3,4-methylenedioxyamphetamine;
N-(2-Methoxyethyl)-3,4-methylenedioxyamphetamine;
N-Hydroxy-3,4-methylenedioxyamphetamine;
N-Propargyl-3,4-methylenedioxyamphetamine;
N-Propyl-3,4-methylenedioxyamphetamine;
3,4-Ethylenedioxy-5-methoxyamphetamine;
2-Methoxy-4,5-diethoxyamphetamine;
2,5-Dimethoxy-4-ethoxyamphetamine;
3-methoxy-4-ethoxy-amphetamine;
3-methoxy-4-allyloxy-amphetamine;
3-methoxy-4-methylamphetamine;
5-Bromo-2,4-dimethoxyamphetamine;
2-bromo-4,5-dimethoxyamphetamine;
5-bromo-2,3-dimethoxyamphetamine;
6-bromo-2,3-dimethoxyamphetamine;
3-bromo-2,6-dimethoxyamphetamine;
2-bromo-3,5-dimethoxyamphetamine;
2,6-dibromo-4,5-dimethoxyamphetamine;
4-bromo-2,5-dimethoxyamphetamine;
5-Methylthio-2,4-dimethoxyamphetamine;
N-Methyl-2,5-dimethoxyamphetamine;
2-methoxy-N-methylamphetamine;
5-hydroxy-2-methoxy-N-methylamphetamine;
N-methyl-3,4,5-trimethoxyamphetamine;
N-methyl-2,4,5-trimethoxyamphetamine;
N-methyl-2,4,6-trimethoxyamphetamine;
4-Bromo-2,5-dimethoxy-N-methylamphetamine;
N-Methyl-4-methoxyamphetamine;
4-methoxy-N-methylamphetamine;
4-methoxy-N,N-dimethylamphetamine;
2-methoxy-N,N-dimethylamphetamine;
N-Methyl-2-methoxy-4,5-methylenedioxyamphetamine;
2,5-dimethoxy-N-methyl-3,4-methylenedioxyamphetamine;
3-Methoxy-4,5-methylenedioxyamphetamine;
2-Methoxy-4,5-methylenedioxyamphetamine;
2-ethoxy-4,5-methylenedioxyamphetamine;
2-Methoxy-3,4-methylenedioxyamphetamine;
4-Methoxy-2,3-methylenedioxyamphetamine;
6-methoxy-2,3-methylenedioxyamphetamine;
2,4-Dimethoxy-5-ethoxyamphetamine;
2,5-Dimethoxy-4-propoxyamphetamine;
4-(n)-butoxy-2,5-dimethoxyamphetamine;
4-(n)-amyl-2,5-dimethoxyamphetamine;
2-Methylthio-4,5-dimethoxyamphetamine;
3,5-dimethoxy-4-(n)-propoxy-amphetamine;
2,3,4,5-Tetramethoxyamphetamine;
3,4-dimethoxy-2-methylthioamphetamine;
2,4-dimethoxy-3-methylthioamphetamine;
2,3-dimethoxy-4-thioamphetamine;
3,4-dimethoxy-5-methylthioamphetamine;
3,4,5-Trimethoxyamphetamine;
2,4,5-Trimethoxyamphetamine;
2,3,4-Trimethoxyamphetamine;
2,3,5-Trimethoxyamphetamine;
2,3,6-Trimethoxyamphetamine;
2,4,6-Trimethoxyamphetamine;
2-Methylthio-3,4-methylenedioxyamphetamine;
3-methoxy-5,4-methylenethiooxyamphetamine
2-methoxy-5,4-methylenethiooxyamphetamine
4,5-Thiomethyleneoxy-2-methoxyamphetamine;
4-Ethyl-5-methoxy-2-methylthioamphetamine;
4-Ethyl-2-methoxy-5-methylthioamphetamine;
5-Methoxy-4-methyl-2-methylthioamphetamine;
2-Methoxy-4-methyl-5-methylthioamphetamine;
2-Methoxy-4-methyl-5-methylsulfinylamphetamine;
3,5-dimethoxy-4-methylthioamphetamine;
3,5-dimethoxy-4-(n)-butylthioamphetamine;
Phentermine;
3,4-methylenedioxyphentermine;
Fenfluramine;
1-amphetamine; and
bupropion.

Along with pharmaceutically acceptable salts and prodrugs of any of the foregoing.

Salts. Active compounds of the invention include pharmaceutically acceptable salts of the foregoing. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Prodrugs. Active compounds of the present invention include prodrugs of the foregoing. "Prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

2. Pharmaceutical Formulations, Administration and Dosage.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active agents or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 1 or 2 to about 50, 100, 200 or 500 milligrams per day, administered once or over two, three or four separate administrations, can be used to carry out the present invention.

Compositions containing an active agent of the invention in combination with an additional antiparkinson's agent are prepared in like manner as described above and techniques that will be apparent to those skilled in the art. Such compositions may be prepared in any suitable unit dosage form including injectable forms and oral dosage forms such as tablets and capsules, as described above. The amount of active agent will depend upon the subject to be treated and the route of administration and can be determined in accordance with known techniques, but in some embodiments is from 0.5 or 1 to 50, 100 or 200 milligrams per dosage form. The amount of the one (or more) additional antiparkinson's agent will depend upon the particular agent, but generally will be from 0.1 or 1 to 200 or 400 milligrams per unit dosage form. See, e.g., U.S. Pat. No. 6,797,732 (levodopa, carbidopa, and COMT inhibitor oral pharmaceutical).

4. Screening Techniques.

The present invention provides a method of screening a compound for antiparkinson's activity. In general, the method comprises: (a) administering a test compound (e.g., orally or by parenteral injection) to a dopamine-depleted dopamine transporter deficient mouse (such as described in U.S. Pat. No. 6,218,595 to Giros et al.), and then (b) detecting the presence or absence of antiparkinson's activity in said mouse. The methods can generally be carried out as described in U.S. Pat. No. 6,218,595 to Giros et al.

In general, the recombinant mouse comprises cells (e.g., including brain tissue cells) containing a pair of genomic dopamine transporter alleles, wherein at least one of said alleles is incapable of expressing endogenous dopamine transporter protein, and wherein there is at least about a 30% reduction in dopamine uptake. The mouse may be a homozygote and both of said alleles are incapable of expressing endogenous dopamine transporter protein; the mouse may be a heterozygote, wherein one of said alleles expresses endogenous dopamine transporter protein. In some embodiments the mouse is an adult.

The mouse is preferably depleted of dopamine sufficient to develop at least one Parkinson's symptom in said mouse. Depletion of dopamine sufficient to develop at least on Parkinson's symptom can be carried out by any suitable technique, such as by administering tyrosine hydroxylase inhibitors such as alpha-methyl-para-tyrosine (αMT) to deplete dopamine (e.g., by parenteral injection) in an amount sufficient to deplete dopamine in the mouse and develop the at least one symptoms. Typical doses thereof are, for example, 50-500 mg/kg. Another approach to depletion is to block the second step in dopamine synthesis by administering L-aromatic acid decarboxylase inhibitors such as 3-hydroxybenzylhydrazine (NSD-1015) (e.g., by parenteral injection of 50-300 mg/kg).

Parkinson's disease in the mouse is characterized by at least one symptom thereof, such as rigidity, akinesia, body tremor, and ptosis (droopy eyelids). These behaviors or symptoms, and beneficial treatment thereof by a test compound being screened, are readily detectable by any suitable technique. For example, akinesia can be assessed by evaluating horizontal locomotor activity and by an "akinesia" test as described herein, rigidity assessed by a catalepsy test, a "grasping" test, and/or a "bracing" test, while tremor and ptosis can be visually determined.

Dopamine depleted mice as described herein are further useful per se for identifying (e.g., by histological techniques such as immunohistochemistry) neuronal pathways and neurotransmitter systems involved in motor functions in conditions of severe dopamine deficiency such as Parkinson's disease.

The present invention is explained in greater detail in the following non-limiting Examples. The following abbreviations are used herein: 5-HT, serotonin; aMT, alpha-methyl-para-tyrosine; DA, dopamine; DAT, dopamine transporter; DAT-KO mice, dopamine transporter knockout mice; DD mice, dopamine-deficient mice; DDD mice, dopamine-deficient DAT-KO mice; IP, intraperitoneal; L-AADC, L-aromatic acid decarboxylase; MAO, monoamine oxidase; NE, norepinephrine; NET, norepinephrine transporter; PD, Parkinson's disease; SC, subcutaneous; SNc, Substantia Nigra Pars Compacta; TA1 receptor, trace amine 1 receptor; TH, tyrosine hydroxylase; VMAT2, vesicular monoamine transporter-2; VTA, ventral tegmental area; WT, wild-type.

EXPERIMENTAL

We report here that the pharmacologic inhibition of the rate-limiting enzyme of DA synthesis, TH, almost immediately depletes brain DA to undetectable levels in DAT-KO mice and induces a transient recapitulation of essentially all PD symptoms for up to 16 h. DA-deficient DAT-KO mice (DDD mice) thus represent an acute PD model that is useful for studying the efficacy of compounds that potentially can restore control of locomotion in the absence of any contribution of the dopaminergic system. By using this approach, we found that several amphetamine derivatives can counteract the behavioral manifestations of severe DA deficiency, suggesting that, in addition to well-known DA-mediated effects, amphetamine-like compounds can also affect motor functions in a DA- and DAT-independent manner.

Materials and Methods

Animals. DAT-KO mice were generated as previously described [11]. Animal care was in accordance with the Guide for Care and Use of Laboratory Animals (National Institutes of Health publication #865-23, Bethesda, Md., United States) with an approved protocol from the Duke University Institutional Animal Care and Use Committee. C57BL/6J3129Sv/J hybrid WT and DAT-KO mice, 3-5 mo old, of both sexes were used. None of animals used in these studies had the neurodegenerative phenotype sporadically observed in DAT-KO mice [60].

Drugs. Drugs or saline (0.9% NaCl) were administered intraperitoneally (IP) or subcutaneously (SC) in a volume of 10 ml/kg. The drags were either from Sigma (St. Louis, Mo., United States) or supplied by the National Institute of Drug Abuse (NIDA). Drugs provided by the NIDA Drug Supply Program included: (±)-MDMA, (+)-MDMA, (±)-6-OH-MDA, (±)-MDA, (±)-MDE, (+)-MDE, (−)-MDE, and AFT (alpha-ethyl-tryptamine acetate).

Neurochemical assessments. Striatal tissue contents of DA and frontal cortical tissue levels of NE were assessed using HPLC-EC (high performance liquid chromatography with electrochemical detection) as described [8]. In vivo microdialysis measurements of striatal extracellular DA levels in freely moving mice were performed at least 24 h after implantation of a microdialysis probe as described previously [50]. Dialysate samples were assayed for DA using HPLC-EC.

Behavioral methods. Locomotor activity of littermate WT and DATKO mice was measured in an Omnitech CCDigiscan (Accuscan Instruments, Columbus, Ohio United States) activity monitor under bright illumination [83]. All behavioral experiments were performed between 10:00 AM and 5:00 PM. Activity was measured at 5-min intervals, To evaluate the effects of drugs on motor behaviors, mice were placed into activity monitor chambers (20×20 cm) for 30 min and then treated with αMT (250 mg/kg IP). A drug or combination of drugs were injected 1 h after αMT administration, and various parameters of locomotor activity were monitored for up to 3 h. In cumulative dosing experiments, animals were treated with increasing doses of drugs after a 1-h interval. For the akinesia test, the mouse is held by the tail so that it is standing on forelimbs only and moving on its own. The number of steps taken with both forelimbs was recorded during a 30-s trial [57]. The presence of catalepsy was determined and measured by placing the animal's forepaws on a horizontal wooden bar (0.7 cm in diameter), 4 cm above the tabletop. The time until the mouse removed both forepaws from the bar was recorded, with a maximum cut-off time of 3 min [53]. In the grasping test of muscular rigidity, the mouse is suspended by its forelimbs on a metal rod (diameter: 0.25 cm) positioned approximately 20 cm above the table. The time the animal remains on the rod (maximum 1 min) was noted [58]. To assess rigidity in a bracing task, the number of steps taken with each forelimb when the mouse is pushed sideways over a distance of 50 cm was recorded [57]. Tremor was scored visually in mice using the rating scale [54]: 0, no tremor; 1, occasional isolated twitches; 2, moderate or intermittent tremor associated with short periods of calm; and 3, pronounced continuous tremor. Ptosis was scored as described [89]: 4, eyes completely closed; 2, half-open eyes; and 0, wide-open eyes; with 1 and 3 indicating intermediate values. The righting reflex was evaluated by turning the mouse onto its back five times. Normal mice immediately turn themselves over, to right themselves onto all four feet. Righting reflex was scored as follows: 0, no impairment; 1, on side one to two times; 2 on side three to four times; 3, on side five times; 4, on back one to two times; 5, on back three to four times; 6, on back five times; 7, sluggish when placed on back; and 8, righting response absent when on back and tail pinched [55].

Data analysis. The data are presented as mean±SEM and analyzed using a two-tailed Student's t-test and one-way analysis of valiance (ANOVA) followed by Dunnet's multiple comparison test or a two-tailed Mann-Whitney U test when appropriate.

Results

A Pharmacologic Approach for Provoking Selective DA Deficiency in DAT-KO Mice.

The ability of α-methyl-p-tyrosine (αMT), a potent irreversible inhibitor of TH [29,45,46], to impede production of brain DA suggests a simple, but straightforward, strategy for producing an acute PD mouse model. However, numerous studies have documented that treatment of normal animals with C/T results only in a relatively slow and partial depletion of DA in brain tissues that is not sufficient for generation of PD-like symptoms [29,45,46]. This limited depletion is based upon how DA is stored. It is believed that the large intraneuronal DA storage pool that normally exists in striatal DA terminals provides sufficient DA to release and recycle back into releasing terminals up to the time when newly synthesized TH starts to regain its functional role [29,45,46]. Thus, in a normal animal, complete depletion of striatal DA is unachievable by TH inhibition alone, and additional depletion of vesicular DA by VMAT2 inhibitors, such as reserpine is required [33,47-49]. Protocols designed for wild-type [WT] mice that use a dual inhibitor strategy (VMAT2 plus TH inhibitor) deplete DA to 1%-2% of control levels [33,47-50], but the levels of other monoamine eurotransmitters that are substrates for VMAT2 are also severely affected. This nonselective targeting of monoaminergic signaling generally results in very complicated phenotypes that are not necessarily reflective of classic PD.

In the absence of any pharmacologic treatment, the intraneuronal vesicular stores of DA in the striatum of DAT-KO mice are already profoundly depleted by at least 20-fold [12]. This selective depletion of DA in dopaminergic terminals of DAT-KO mice, as well as analogous depletion observed in mice lacking NET [51] or serotonin transporter [52] with NE and scrotonin (5-HT), respectively, reflects the critical role of transporter-mediated recycling in the maintenance of intracellular storage pools [13] With loss of the major intracellular storage pool of DA in DAT-KO mice, both the intracellular and extracellular levels of DA in the striatum become critically dependent upon ongoing, DA synthesis. Therefore in DAT-KO mice, acute TH inhibition alone by αMT is sufficient to induce profound depletion of DA [12,13,37].

To explore this phenomenon in detail, we first measured the time-course of striatal DA depletion in DAT-KO and control mice following treatment with αMT (FIG. 1). In agreement with previous studies [13], we observed that in untreated DAT-KO mice, striatal tissue levels of DA were about 20-fold lower than in WT controls (FIG. 1A). The systemic administration of αMT (250 mg/kg IP) to DAT-KO mice produced rapid (15 min) and virtually complete (down to 5% of control levels in DAT-KO mice that is equivalent to less than 0.2% of WT control levels) depletion of striatal DA. In contrast, in WT mice the same treatment resulted in a relatively slow (4 h) depletion of only 60% of striatal tissue DA (FIG. 1B). The duration of the depletion in DAT-KO mice was extensive, lasting up to 16 h, until a recovery of DA, related to the de novo synthesis of TH, occurs [29,45]. Notably, the rate of recovery of striatal DA levels was approximately the same in WT and DAT-KO mice.

Because DA itself serves as a precursor for neuronal production of NE in NE neurons, the inhibition of TH should also impact NE production. To test the impact of TH inhibition on the NE system, the frontal cortex tissue NE concentrations were measured in WT and DAT-KO mice. As opposed to the DAT, NET expression is not altered in DATKO mice so that the storage pool, which is by far the predominant reservoir of NE in NE-enriched regions such as the frontal cortex, should not be significantly altered in these mutants. Accordingly, the levels of NE in the frontal cortex tissue of untreated DAT-KO mice did not vary from that of WT mice (FIG. 1C). Furthermore, αMT (250 mg/kg IP) treatment induced similar NE depletion in WT and DAT-KO mice by about 60% in 8 h after treatment. Importantly, the rates of partial NE depletion and recovery were almost identical between WT and DAT-KO mice (FIG. 1D). Thus, TH inhibition in DAT-KO mice induces rapid severe depletion of DA, but only partially and slowly affects NE, indicating, selectivity of this marked depletion to neurons expressing the DAT.

In order to demonstrate that targeting of TH by αMT depletes the functional extracellular pool of DA in living animals, we measured extracellular levels of striatal DA in freely moving mice by in vivo microdialysis. In agreement with total tissue DA data, αMT treatment essentially eliminated extracellular DA levels in DAT-KO mice (FIG. 1F), whereas only a partial decrease was observed in WT mice. (FIG. 1E). Thus, both intracellular and extracellular DA levels in the striatum of DAT-KO mice are critically dependent upon ongoing synthesis.

DA Depletion in DAT-KO Mice Results in a Loss of Motor Control.

It is well known that DA plays a pivotal role in the control of various aspects of locomotor behaviors. Severe depletion of DA in αMT-treated DAT-KO mice results in a very specific akinetic phenotype (not shown). The DA-depleted DAT-KO mice (DDD mice) become akinetic almost immediately after treatment, in contrast to the essentially normal motor function displayed by αMT-treated WT mice. Moreover, DDD mice develop extreme rigidity, body tremor, and ptosis (droopy eyelids). These behaviors are evident on several tests (FIG. 2). Akinesia was assessed by evaluating horizontal locomotor activity (FIGS. 2A and 2B) and by an "akinesia" test (FIG. 2C); rigidity assessed by a catalepsy test (FIG. 2D), a "grasping" test (FIG. 2E), and a "bracing" test (FIG. 2F); whereas tremor (FIG. 2G) and ptosis (FIG. 2H) were visually determined [3,53-58]. These behaviors were analyzed in WT and DAT-KO mice for 4 h after of αMT treatment when depletion of DA is most severe in DAT-KO mice but with relatively minor effect on NE levels (see FIG. 1). In all these measures DDD mice differed significantly from their WT littermates or saline-treated controls. Importantly, these abnormal behaviors in DDD mice, with the exception of ptosis, became maximal during the 30- to 60-min period following αMT exposure, thus correlating with the rate of DA depletion. Ptosis developed substantially later (FIG. 2H), suggesting an additional contribution of NE depletion to the full magnitude of this response [59]. Importantly, the righting reflex of DDD mice was normal at all time periods analyzed (FIG. 2I), indicating that this akinesia is not related to global sedation but rather to deficient movement control. It should be noted also that this global phenotype, which might be viewed as "freezing," can be on some occasions temporarily disrupted by an acoustic startle or other stressful stimulus. However, after manifesting, a few movements, the animals return to an akinetic state (data not shown). Strikingly, DOD mice, when placed in water, were able to swim with periods of floating and active swimming for at least a 3-min period (not shown), indicating that under certain conditions, movement can occur essentially without DA. Finally, in agreement with neurochemical data (see FIG. 1B), the recovery from this profound akinetic phenotype in DDD mice occurs approximately 16-24 h following treatment (FIG. 2J). The full recovery of animals allows repeated treatment with αMT, and, in facts, DAT-KO mice chronically treated with αMT (100 mg/kg, IP, once every 3 d) for a period of 40 wk showed no negative consequences [60].

L-DOPA and Nonselective DA Agonists Restore Motor Activity in DDD Mice.

The locomotor restoring effects exhibited by L-DOPA and DA agonists in various models of DA deficiency form one of the best-established paradigms in neuroscience [3,15,45,61]. As expected, high doses of L-DOPA alone (FIG. 3A), or lower doses of L-DOPA given along with carbidopa (FIG. 3B-3D) to reduce its peripheral metabolism via L-AADC inhibition, effectively restore locomotion in DDD mice. In fact, these treatments temporarily restore locomotion to the levels observed in untreated DAT-KO mice (FIG. 3A-39), which are normally at least 10 times more active than WT mice when placed into a novel environment [11,13]. Other manifestations associated with DA deficiency as described in FIG. 2 were also essentially completely reversed (data not shown).

Efficacy of exogenous direct DA agonists was also tested in this model. Although the nonselective D1/D2 DA receptor agonists apomorphine and pergolide were somewhat effective in inducing forward locomotion (FIGS. 3E and 3F), the activity levels of DDD mice following these treatments were substantially lower than those induced by L-DOPA. Strikingly, the selective D1 DA receptor agonist (+)-SKF81297 and D2 DA receptor agonists, bromocriptine and quinpirole, were ineffective in inducing forward locomotion when administered separately (FIG. 3G-3I). However, the combined administration of the D1 and D2 agonists (+)-SKF81297 plus quinpirole restored movement and induced forward locomotion (FIG. 4J), supporting the well-established cooperative interaction of D1 and D2-like DA receptors in locomotor activity [62].

Movement-Restoring Actions of Amphetamine Derivatives in DDD Mice.

The loss of DA signaling that creates the motor symptoms of PD occurs upstream of many nondopaminergic pathways. This suggests that activation or inhibition of some of these downstream neuronal circuits could potentially reverse the motor deficits independent of restoration of upstream DA activity. We, therefore, tested several non-dopaminergic compounds that potentially could reverse the consequences of severe DA deficiency in DDD mice (data not shown). Many of these compounds have been found to be effective in restoring some aspects of movement control in one or another experimental animal model of PD and/or in PD patients [21,26,27, 48,49]. However, in DDD mice none of the drugs were effective in restoring the major aspects of movement control required for forward locomotion (distance traveled). Although it is likely that the lack of locomotor effects of these drugs in DDD mice is related to an unprecedented level of DA depletion in these mice, it should be emphasized that in our studies only a few doses or combinations of drugs were tested. Furthermore, several treatments, although not inducing forward locomotion per se, were, nevertheless, somewhat effective in reversing other manifestations of DA deficiency. For example, the NMDA receptor antagonist ME-801 was able to reduce rigidity and promote weak, disorganized movement that however did not result in a significant increase in forward locomotion (data not shown). Synthetic amino acid L-DOPS (L-threo-3,4-dihydroxyphenylserine), which is decarboxylated to NE by L-AADC, selectively reversed ptosis in DDD mice. Cumulative dosing experiments revealed ptosis scores (measured 1 h after each treatment) of 2.50±0.28 after 100 mg/kg, 0 after 200 mg/kg, and 0 after 400 mg/kg IP of L-DOPS (n=4), whereas corresponding values for saline-treated controls (n=6) were 3.3±0.3, 3.7±0.2, and 3.7±0.2, respectively. Effects of 200 and 400 mg/kg of L-DOPS on ptosis in DDD mice were significantly different as compared to respective control values (p<0.05, Student's t-test) supporting an important role of NE in this behavioral manifestation [59]. Similarly, high doses of the trace amine beta-phenylethylamine [44,63] (with or without concomitant inhibition of MAO) did not induce forward locomotion, but did promote weak stereotypic reactions, such as headweaving and sniffing (data not shown). Further investigations will be required to fully evaluate the efficacy of these drugs in DDD mice.

Unexpectedly, this initial screening revealed a potent effect of amphetamine derivatives on behavioral manifestations of DDD mice. High doses of d-amphetamine, d-methamphetamine, 4-chloro-amphetamine, phentermine, (±)-MDE ((±)-N'-ethyl-3,4-methylenedioxyamphetamine HCl), (+)-MDE ((+)-N-ethyl-3,4-methylenedioxyamphetamine HCl), (−)-MDE ((−)-N-ethyl-3,4-methylenedioxyamphetamine HCl), (±)-MDA ((±)-3,4-methylenedioxyamphetamine HCl). (±)-6-OH-MDA ((6)-6-hydroxy-3,4-methylenedioxyamphetamine HCl), (±)-MDMA ((±)-3,4-methylenedioxymethamphetamine HCl), and (+)-MDMA ((+)-3,4-methylenedioxymethamphetamine HCl) were effective in reducing manifestations of akinesia and rigidity in DDD mice as detected in the catalepsy, grasping, and akinesia tests (FIG. 4A-4C). Similar effects were observed with other amphetamine derivatives-L-amphetamine, bupropion, DOI, isomers of fenfluramine (see Table 1). However none of these drugs (with the exception of (+)-MDMA, see below) was effective in restoring movement control sufficiently to induce forward locomotion (data not shown).

DA-Independent Locomotor Effects of (+)-MDMA in DD Mice.

Among amphetamine derivatives, the most effective compound to counteract manifestations of akinesia and rigidity in DDD mice was (+)-MDMA (FIG. 4A-4C). Thus, we tested (+)-MDMA in locomotor assay at even higher doses than those indicated in Table 1. As presented in FIG. 5A-5C, (+)-MDMA at high doses was able to induce significant forward locomotion in DDD mice as measured by distance traveled in a locomotor activity test. This locomotor action of (+)-MDMA was observed in both cumulative (FIG. 5A) and single dose (FIGS. 5B and 5C) treatments. In cumulative dosing experiments, a first treatment with 30 mg/kg of (+)-MDMA was not effective, but the subsequent administration of 60 mg/kg induced significant forward locomotion (FIG. 5A) as well as reversal of other behavioral manifestations (see FIG. 4A-4C) in DDD mice. Finally, testing of various single doses clearly showed a dose-dependence of the locomotor effect of (+)-MDMA in DDD mice (FIG. 5C). The locomotor stimulating effect of amphetamine and its derivatives are classically thought to result from the massive efflux of DA from presynaptic DA terminals via a mechanism including displacement of DA form vesicular storage and reversal of DAT-mediated DA transport [7,38-40]. However, in DDD mice, there is only a minimal amount of DA remaining (<0.2%) and the lack of the DAT precludes the possibility of amphetamine-mediated DA efflux. In fact, in vivo microdialysis studies confirmed that (+)-MDMA, at the effective dose necessary to induce significant locomotor activation in DDD mice, did not produce any detectable increase in striatal extracellular DA (FIG. 5D). Moreover, this locomotor stimulation by (+)-MDMA was not inhibited by simultaneous blockade or D1/D2 DA receptors when DDD mice were pretreated with a combination of the D1 and 2 DA receptor antagonists, SCH23390 and raclopride (FIG. 5C). Similarly, this pretreatment did not prevent the effects of amphetamine and phentermine on the akinesia and rigidity in DDD mice in grasping and akinesia tests (not shown).

In contrast, the same D1/D2 DA receptor blockade completely abolished the locomotor stimulating effects of L-DOPA/carbidopa (50/50 mg/kg IP) in DDD mice (not shown). Taken together, these data indicate that (+)-MDMA can affect movement control in a DA-independent manner and, most importantly, provide a proof-of-principle that pharmacologic activation of nondopaminergic neuronal pathways may be sufficient to restore movement even in the virtual absence of DA neurotransmission.

It should be noted that the locomotor-stimulating effect of (+)-MDMA in DDD mice was observed only after high doses of the drug, which may be potentially neurotoxic [64]. However, the lack of the DAT renders dopaminergic neurons in DATKO mice significantly less sensitive to the neurotoxic effects of amphetamines, such as methamphetamine [65], as well as to MPTP (1-methyl-4-phenyl-1,2,3,6-tetrahydropyridine) [66,67]; thereby providing a unique opportunity to evaluate effects to large doses of amphetamines that would be impossible in normal animals [38]. It should be mentioned also that mice are generally less sensitive to MDMA neurotoxicity, particularly with regards to the serotonergic system [68]. Nevertheless, to directly evaluate the neurotoxic potential of MDMA in DAT-KO mice, we treated DAT-KO and WT mice with an established neurotoxic regimen of (±)-MDMA administration (4 injections of 20 mg/kg IP, every 2 h) [69] and assessed striatal tissue DA and 5-HT levels 7 d later. As might be expected, no significant differences in both DA and 5-HT levels were found between (±)-MDMA-treated and saline-treated DAT-KO mice (saline-treated DAT-KO mice (n=6): DA, 0.53±0.03 ng/mg tissue; 5-HT, 0.36±0.03 ng/mg tissue; (±)-MDMA-treated DAT-KO mice (n=7): DA, 0.58±0.04 ng/mg tissue; 5-HT, 0.40±0.02 ng/mg tissue), whereas the same regimen of treatment resulted in lethality of all treated WT mice (n=7).

Furthermore, to test whether the locomotor-stimulating effect of (+)-MDMA may be evident under certain conditions with lower (nonneurotoxic) doses of the drug, we coadministered (+)-MDMA with a minimally effective dose of L-DOPA/carbidopa (10/10 mg/kg, IP.). As shown in FIG. 5E, a potent synergistic effect of L-DOPA/carbidopa and (+)-MDMA was observed. Furthermore, similar effects were observed with lower doses of d-amphetamine and d-methamphetamine (FIG. 5F). Thus, a DA-independent locomotor effect of amphetamines can be markedly enhanced with additional dopaminergic stimulation. It is also important to note that in a similar experiment, MAO inhibitor deprenyl (5, 10, or 20 mg/kg IP) failed to potentiate the effects of LDOPA/carbidopa (data not shown), indicating that this effect is not related to the well-known MAO-inhibiting action of amphetamines [38].

Nomifensine, but Not GBR12909 Affects Rigidity and Akinesia in DDD Mice.

Finally, to evaluate the potential of other TA1 receptor ligands for their ability to affect motor control in DDD mice, we elected to compare the effects of two potent DAT blockers that have been shown to be markedly different with regards to their activity at TA1 receptor. It has been recently reported that the mixed DAT and NET inhibitor nomifensine can also potently activate TA1 receptor whereas selective DAT blocker GBR12909 completely lacks the ability to interact with TA1 receptor [42]. In DDD mice, both nomifensine and GBR12909 at doses tested (cumulative treatment with 10 and 30 mg/kg IP) were not effective in inducing forward locomotion or reversing catalepsy (data not shown). Nevertheless, nomifensine significantly reduced akinesia and rigidity in grasping and akinesia tests (FIGS. 6A and 6B), whereas no such effects were observed with equivalent doses of GBR12909 (FIGS. 6A and 6B).

Discussion

In this study we demonstrate that inhibition of DA synthesis in DAT-KO mice represents a straightforward approach for developing an acute model of severe DA deficiency exhibiting a characteristic behavioral phenotype that can be utilized for testing perspective anti-PD treatments. Furthermore, these observations provide functional evidence for an important role of DAT-mediated recycling mechanism in the maintenance of intraneuronal DA. Finally, the novel DAT- and DA-independent locomotor action of amphetamines identified in these mice directly demonstrates the possibility of movement in a DA-independent manner.

Role of DAT-Mediated DA Recycling in the Maintenance of Intraneuronal DA Storage.

DAT is commonly known as a major regulator of the duration and intensity of extracellular DA signaling. However the important role of DAT in the control and maintenance of the intraneuronal DA storage pool frequently remains overlooked. It is generally assumed that the intraneuronal storage of DA is replenished primarily from newly synthesized DA with some contribution from recycled DA. However, several lines of evidence support a predominant role of DATmediated recycling of DA for the maintenance of the large storage pool in DA terminals. First, mice lacking the DAT display dramatically decreased (20-fold) striatal tissue DA content, reflecting predominantly intraneuronal DA concentrations. Second, as we demonstrate in the present study, the remaining DA in all compartments is extremely sensitive to TH inhibition. Furthermore, pharmacologic studies have shown that significant DA depletion may occur after administration of DAT inhibitors, particularly after chronic drug treatment [13]. Importantly, in the frontal cortex, where DAT levels are normally low in comparison to the striatum, tissue DA concentration is also low and can be more significantly affected than in the striatum by αMT [70]. It is likely that the newly synthesized DA does not contribute directly to the large storage pool of DA in nigrostriatal terminals, but rather contributes to it indirectly via released and recycled DA. Thus, a cooperative function of both DA synthesis and transporter-mediated recycling processes is necessary for the maintenance of normal presynaptic monoamine concentrations.

A Novel Acute Mouse Model of Severe DA Deficiency, DA-Depleted DAT-KO (DDD) Mice.

By using a combination of genetic and pharmacologic approaches we have developed a novel acute mouse model of severe DA deficiency, DDD mice. The lack of an active recycling mechanism in DAT-KO mice results in a profound depletion of intraneuronal concentrations of DA leaving the remaining DA entirely dependent on ongoing synthesis. As a result, inhibition of DA synthesis essentially eliminates striatal DA in these mice leading to the extreme behavioral manifestations. In fact, DDD mice demonstrate a unique set of behaviors that reproduces symptoms of PD with high fidelity. Thus, the lack of DA combined with the striking and highly reproducible behavioral phenotype in these mice can be used as an excellent tool to evaluate the potential of drugs that can affect locomotion in a DA-independent manner.

Furthermore, by adapting the dose of αMT to produce various degrees of DA depletion, these mice can also be employed to find novel approaches to restore movement under conditions of partially impaired DA transmission that might be more relevant to most PD cases. Several rodent models have been developed to understand pathological processes leading to PD and/or to screen for novel therapeutic strategies [29,30,71]. These models either recapitulate the loss of DA through pharmacologic or genetic manipulation, or recapitulate the neurodegenerative process through administration of selective neurotoxins and, recently, through mutations of specific proteins. However, in many of these models only incomplete and highly variable levels of DA depletion are achieved often precluding an accurate recapitulation of the neurological manifestations of PD. This poor behavioral expression of PD-related behaviors generally results in high level of false-positive results in drug screening tests in general, and particularly in those attempted to identify non-DA therapies [72].

Among several genetic mouse models of DA deficiency available today [73,74], the most effective was developed by inactivation of TH in DA neurons (DA-deficient [DD mice]) [3,75-80]. DD nice have provided important insights into the role of DA in movement control, feeding, and reward. This mutation results in severely impaired movement and feeding, which become apparent at 10 d and leads to death by 30 d. To maintain viable mice with the ability to move and feed requires daily treatment with L-DOPA, which results in an oscillation of striatal DA from about 1% to 10% over 24 h [77,81]. Many behavioral manifestations observed in DDD mice in this study, such as rigidity and akinesia, were observed previously in DD mice [3,76,79]. Importantly, both of these models showed temporal locomotor reactivity to stress and demonstrate normal righting reflex and ability to swim, indicating that certain movements may occur in a DA-independent manner.

Despite these similarities, some important differences were noted between these two genetic models of severe DA dysfunction. In DD mutant mice, a lack of TH resulting in permanently decreased DA signaling, as well as daily treatments with L-DOPA render these mice extremely supersensitive to DA stimulations [81], whereas excessive DA signaling in DAT-KO mice results in compensatory downregulation (but non-uniform) of DA receptors [11,13]. This may explain why certain behavioral manifestations of DA deficiency such as rigidity and akinesia may be more robust in DDD mice, whereas tremor was not observed in DD mutants [3,76]. Furthermore, efficacy of L-DOPA and DA agonists are remarkably higher in DD in comparison to DDD mice [3,76, 81]. Additionally, several other drugs, such as caffeine and N-methyl-D-aspartate receptor antagonist MK-801, that are able to induce locomotion in DD mutant is [75,80] are not effective in DDD mice (not shown). In fact, down-regulation of DA receptor responsiveness combined with the extreme level of DA depletion in DDD mice may favor these mice as a very conservative approach for evaluating drugs that can affect locomotion in a DA-independent manner. Furthermore, rapid and effective elimination of DA in DDD mice may provide a simple in vivo approach to study DA receptor signaling [82] and/or to define neuronal circuitry involved in locomotor control [83].

DA-Independent Locomotor Action of Amphetamines.

Intriguingly, in both DD and DDD mice d-amphetamine was effective in restoring at least some aspects of locomotor behaviors. In DD mice, d-amphetamine (5 mg/kg P) induced potent locomotor activation essentially up to the levels observed in WT controls. At the same time, a second treatment 2 h later by the same dose of the drug failed to induce locomotion in DD mice suggesting that this effect is dependent upon residual (after L-DOPA administration) DA which might be depleted by the first treatment with the drug [76]. In DDD mice, d-amphetamine itself was not able to induce forward locomotion at doses up to 60 mg/kg, but it produced significant effects on other manifestations of DA deficiency. Moreover, co-administration of relatively moderate doses of amphetamine (15 and 20 mg/kg) with a subthreshold dose of L-DOPA resulted in a marked locomotor activation of DDD mice. Thus, some DA tone seems to be necessary to express the full magnitude of locomotor activation by amphetamine, but it is evident that there is a DA-independent component of action that contributes to the overall effect of the drug. Further evidence for this idea relates to the fact that many other amphetamine derivatives are also active in reversing certain behavioral manifestations in DDD mice. Strikingly, both single and repeated treatment with (+)-MDMA was effective in inducing forward locomotion essentially without any contribution of DA. It is important to note that a potent anticataleptic effect of MDMA in haloperidol-treated rats [84] and antiakinetic effects in 6-OH-DA-lesioned rats [85] and MPTP-treated monkeys [64] have been recently reported. The present observations support these findings and suggest that these actions are not unique to MDMA but may be extended to other amphetamines. Further characterization of these unexpected effects of amphetamines may provide a novel framework in the search for potential anti-Parkinsonian drugs.

Amphetamine derivatives are known mainly as indirect enhancers of monoaminergic (DA, NE, and 5-HT) transmission via complex interactions with the plasma membrane monoamine transporters and the vesicular storage of these monoamines [7,10,12,38,39]. It should be reiterated that a lack of DAT in DAT-KO mice excludes the possibility of major effects of amphetamines on DAT-mediated DA efflux from presynaptic DA stores [40]. Furthermore, a blockade of D1/D2 DA receptors was ineffective in preventing the locomotor stimulating action of (+)-MDMA. Thus, it is virtually impossible that the observed effects of MDMA and other amphetamines in DDD mice are directly related to DA transmission. Although it is possible that this effect may be due to transporter-mediated action of amphetamines on NE or 5-HT transmission [38,40,86], it should be noted that among several NE- and 5-HT-related drugs tested (desipramine, clonidine, the NE precursor DOPS, fluoxetine, 5-methoxy-N,N-dimethyltryptamine,5-methyl-N,N-dimethyltryptamine, b-ethyltryptamine, and 5-HT1B agonist RU24969), none were effective in DDD mice in tests of forward locomotion or akinesia and rigidity (data not shown). Similarly, no locomotor effect of MAO-A or MAO-B inhibitors was observed in these mice, indicating that the locomotor effect of amphetamines may not be explained by MAO-inhibitory action [38].

Furthermore, it should be underlined that locomotor actions of amphetamines observed in DDD mice occur at doses that are much higher than necessary to induce classic DA transporter mediated effects [10,38,83].

Amphetamines share close structural similarity with an endogenous trace amine of unknown function β-phenylethylamine [87]. Amphetamines and β-phenylethylamine similarly interact with the plasma membrane monoamine transporters to elevate extracellular monoamine concentrations [63].

Intriguingly, recent evidence indicates that many amphetamine derivatives, including MDMA, may also act directly as agonists of trace amine TA1 receptors, that are known to be activated by β-phenylethylamine [42,88]. Several members of the family of trace amine receptors have been identified, however little is known about the pharmacology and functional role of these receptors in mammalian physiology [43, 44,63]. It is reasonable to suggest that activation of TA1 receptors [42] or other trace amine receptors may provide a potential mechanism for DA-independent locomotor effect of MDMA and amphetamines in DDD mice. In line with this hypothesis, we observed that the DAT blocker nomifensine that can activate TA1 receptor, but not GBR12909 which is devoid this activity [42], is able to affect motor control in DDD mice, It should be noted, however, that in our initial exploration in DDD mice, we did not observe clear locomotor effects for any trace amine tested; but only a few doses, routes of administration, and combinations with enzyme inhibitors were investigated. Further detailed investigations will be needed to clarify the mechanism of locomotor action of amphetamines in DDD mice.

The effects of additional isopropylamine derivatives in DA-depleted DAT-KO (DDD) mice are also given in Table 1 below.

CONCLUSIONS

In summary, these results provide additional functional evidence for the critical role of DAT in the maintenance of DA storage in presynaptic terminals. Rapid and effective abolishment of DA by inhibition of DA synthesis in DAT-KO mice provides a novel approach to develop severe DA deficiency that might be used to identify neuronal mechanisms involved in motor control in the absence of DA. Amphetamines are capable of affecting neuronal systems involved in motor control through mechanisms independent of DAT, in particular, and DA in general.

TABLE 1

Effects of additional isopropylamine derivatives in DA-depleted DAT-KO (DDD) mice.

| Drugs | Dose, mg/kg, i.p. (number of mice) | Grasping test (sec) | | | Catalepsy (sec) | | | Akinesia (steps) | | |
|---|---|---|---|---|---|---|---|---|---|---|
| | | 1 h | 2 h | 3 h | 1 h | 2 h | 3 h | 1 h | 2 h | 3 h |
| Saline | (6) | 52 ± 6 | 60 ± 0 | 60 ± 0 | 180 ± 0 | 180 ± 0 | 180 ± 0 | 4 ± 2 | 5.5 ± 2 | 2 ± 1 |
| L-Amphetamine | 40 and 40 (6) | 25 ± 8* | 9 ± 3* | | 180 ± 0 | 99 ± 36 | | 21 ± 14 | 29 ± 5* | |
| Bupropion | 30 and 60 (8) | 25 ± 6* | 16 ± 3* | | 92 ± 29* | 123 ± 28 | | 16 ± 7 | 29 ± 11 | |
| (±)-DOI | 5, 20 and 50 (6) | 28 ± 8* | 29 ± 6* | 29 ± 9* | 180 ± 0 | 180 ± 0 | 180 ± 0 | 0 ± 0 | 4 ± 1 | 12 ± 2* |
| | 80 (6) | 10 ± 4* | 19 ± 5* | | 180 ± 0 | 180 ± 0 | | 14 ± 5 | 20 ± 8 | |
| (+)-Fenfluramine | 30 and 60 (14) | 19 ± 4* | 9 ± 4* | | 176 ± 4 | 113 ± 23 | | 7 ± 2 | 21 ± 3* | |
| (−)-Fenfluramine | 30 and 60 (8) | 9 ± 4* | 4 ± 1* | | 157 ± 14 | 104 ± 31 | | 36 ± 5* | 28 ± 5* | |
| (±)-Fenfluramine | 30 and 60 (8) | 11 ± 4* | 8 ± 4* | | 144 ± 25 | 138 ± 28 | | 44 ± 8* | 32 ± 6* | |

Mice were treated with αMT (250 mg/kg, i.p.) and 1 h after drugs or saline were injected. In cumulative dosing experiments, animals were treated with different doses of a drug every 1 h and were tested 1 h after administration.
*p < 0.05 vs corresponding time point in saline-treated controls (two-tailed Student's t-test).

REFERENCES

1. Molinoff P B, Axelrod J (1971) Biochemistry of catecholamines. Annu Rev Biochem 40: 465-500.
2. Carlsson A, Waters N, Holm-Waters S, Tedroff J, Nilsson M, et al. (2001) Interactions between monoamines, glutamate, and GABA in schizophrenia: New evidence Annu Rev Pharmacol Toxicol 41: 237-260.
3. Zhou Q Y, Palmiter R D (1995) Dopamine-deficient mice are severely hypoactive, adipsic, and aphagic. Cell 83: 1197-1209.
4. Dahlstrom A, Fuxe K (1964) Localization of monoamines in the lower brain stem. Experientia 20: 398-399.
5. Lindvall O, Bjorklund A (1974) The organization of the ascending catecholamine neuron systems in the rat brain as revealed by the glyoxylic acid fluorescence method. Acta Physiol Scand Suppl 412: 1-48.
6. Ungerstedt U (1971) Stereotaxic mapping of the monoamine pathways in the rat brain. Acta Physiol Scand Suppl 367: 1-48.
7. Fon E A, Pothos E N, Sun B C, Killeen N, Sulzer D, et al. (1997) Vesicular transport regulates monoamine storage and release but is not essential for amphetamine action. Neuron 19: 1271-1283.
8. Wang Y M, Gainetdinov R R, Fumagalli F, Xu F, Jones S R, et al. (1997) Knockout of the vesicular monoamine transporter 2 gene results in neonatal death and supersensitivity to cocaine and amphetamine. Neuron 19: 1285-1296.
9. Missale C, Nash S R, Robinson S W, Jaber M, Caron M G (1998) Dopamine receptors: From structure to function. Physiol Rev 78: 189-225.
10. Amara S G, Sonders M S (1998) Neurotransmitter transporters as molecular targets for addictive drugs. Drug Alcohol Depend 51: 87-96.
11. Giros B, Jaber M. Jones S R, Wightman R M, Caron M G (11996) Hyperlocomotion and indifference to cocaine and amphetamine in mice lacking the dopamine transporter. Nature 379: 606-612.
12. Jones S R, Gainetdinov R R, Jaber M, Giros B, Wightman R M, et al. (1998) Profound neuronal plasticity in response to inactivation of the dopamine transporter. Proc Natl Acad Sci USA 95: 4029-4034.
13. Gainetdinov R R, Caron M G (2003) Monoamine transporters; From genes to behavior. Annu Rev Pharmacol Toxicol 43: 261-284.
14. Carlsson A (1972) Biochemical and pharmacological aspects of Parkinsonism. Acta Neurol Scand Suppl 51: 11-42,
15. Hornykiewicz O (2002) L-DOPA: From a biologically inactive amino acid to a successful therapeutic agent. Amino Acids 23: 65-70.
16. Wichmann T, DeLong M R (2003) Functional neuroanatomy of the basal ganglia in Parkinson's disease. Adv Neurol 91: 9-18.
17. Graybiel A M (2000) The basal ganglia. Curr Biol 10: R509-R511.
18. Fahn S (2003) Description of Parkinson's disease as a clinical syndrome. Ann N Y Acad Sci 991: 1-14.
19. DeLong M R, Wichmann T (2001) Deep brain stimulation for Parkinson's disease. Ann Neurol 49: 142-143.
20. Isacson O, Bjorklund L M, Schumacher J M (2003) Toward full restoration of synaptic and terminal function of the dopaminergic system in Parkinson's disease by stem cells. Ann Neurol 53 Suppl 3: S135-S146; discussion S146-S138.
21. Fahn S (1998) Medical treatment of Parkinson's disease. J Neurol 245: P15-P24.
22. Carlsson A, Lindqvist M, Magnusson T (1957) 3,4-Dihydroxyphenylalanine and 5-hydroxytryptophan as reserpine antagonists. Nature 180: 1200.
23. Birkmayer W, Hornykiewicz O (1961) [The L-3,4-dioxyphenylalanine (DOPA)-effect in Parkinson-akinesia.]. Wien Klin Wochenschr 73: 787-788.
24. Youdim M B, Lavie L (1994) Selective MAO-A and B inhibitors, radical scavengers and nitric oxide synthase inhibitors in Parkinson's disease. Life Sci 55: 2077-2082.
25. Jenner P (2002) Pharmacology of dopamine agonists in the treatment of Parkinson's disease. Neurology 58: S1-S8.
26. Hornykiewicz O (2001) Chemical neuroanatomy of the basal ganglia—normal and in Parkinson's disease. J Chem Neuroanat 22: 3-12.
27. Silverdale M A, Fox S H, Crossman A R, Brotchie J M (2003) Potential nondopaminergic drugs for Parkinson's disease. Adv Neurol 91: 273-291.
28. Kase H, Aoyama S. Ichimura M, Ikeda K, Ishii A, et al. (2003) Progress in pursuit of therapeutic A2A antagonists: The adenosine A2A receptor selective antagonist KW6002: Research and development toward a novel nondopaminergic therapy for Parkinson's disease. Neurology 61: S97-S100.
29. Schultz W (1982) Depletion of dopamine in the striatum as an experimental model of Parkinsonism: direct effects and adaptive mechanisms. Prog Neurobiol 18: 121-166.
30. Zigmond M J, Stricker E M (1984) Parkinison's disease: Studies with an animal model. Life Sci 35: 5-18.
31. Langston J W, Langston E B, Irwin 1 (1984) MPTP-induced parkinsonism in human and non-human primates—clinical and experimental aspects. Acta Neurol Scand Suppl 100: 49-54.

32. Carlsson A (1987) Development of new pharmacological approaches in Parkinson's disease. Adv Neurol 45: 513-518.
33. Gerlach M, Riederer P (1996) Animal models of Parkinson's disease: an empirical comparison with the phenomenology of the disease in man. J Neural Transm 103: 987-1041.
34. Dawson T M (2000) New animal models for Parkinson's disease. Cell 101: 115-118.
35. Dauer W, Przedborski S (2003) Parkinson's disease: Mechanisms and models. Neuron 39: 889-909.
36. Levine M S, Cepeda C, Hickey M A, Fleming S M, Chesselet M F (2004) Genetic mouse models of Huntington's and Parkinson's diseases: illuminating but imperfect. Trends Neurosci 27: 691-697.
37. Benoit-Marand M, Jaber M, Gonon F (2000) Release and elimination of dopamine in vivo in mice lacking the dopamine transporter: functional consequences. Eur J Neurosci 12: 2985-2992.
38. Seiden L S, Sabol K E, Ricaurte G A (1993) Amphetamine: Effects on catecholamine systems and behavior. Annu Rev Pharmacol Toxicol 3: 639-677.
39. Sulzer D. Chen T K, Lau Y Y, Kristensen H, Rayport S, et al. (1995) Amphetamine redistributes dopamine from synaptic vesicles to the cytosol and promotes reverse transport. J Neurosci 15: 4102-4108.
40. Jones S R, Gainetdinov R R, Wightman R M, Caron M G (1998) Mechanisms of amphetamine action revealed in mice lacking the dopamine transporter. J Neurosci 18: 1979-1986.
41. Budygin E A, Brodie M S, Sotnikova T D. Mateo Y, John C E. et al. (2004) Dissociation of rewarding and dopamine transporter mediated properties of amphetamine. Proc Natl Acad Sci USA 101: 7781-7786.
42. Bunzow J R, Sonders M S, Arttamangkul S, Harrison L M, Zhang G, et al. (2001) Amphetamine, 3,4-methylenedioxymethamphetamine, lysergic acid diethylamide, and metabolites of the catecholamine neurotransmitters are agonists of a rat trace amine receptor. Mol Pharmacol 60: 1181-1188.
43. Premont R T, Gainetdinov R R, Caron M G (2001) Following the trace of elusive amines. Proc Natl Acad Sci USA 98: 9474-9475.
44. Branchek T A, Blackburn T P (2003) Trace amine receptors as targets for novel therapeutics: Legend, myth and fact. Curr Opin Pharmacol 3: 90-97.
45. Carlsson A (1975) Drugs acting through dopamine release. Pharmacol Ther [B] 1: 401-405.
46. Carlsson A (1975) Monoamine precursors and analogues. Pharmacol Ther [B] 1: 381-392.
47. Carlsson M, Carlsson A (1989) Dramatic synergism between MK-801 and clonidine with respect to locomotor stimulatory effect in monoaminedepleted mice. J Neural Transm 77: 65-71.
48. Carlsson M, Carlsson A (1990) Interactions between glutamatergic and monoaminergic systems within the basal ganglia-implications for schizophrenia and Parkinson's disease. Trends Neurosci 13: 272-276.
49. Carlsson M, Svensson A, Carlsson A (1991) Synergistic interactions between muscarinic antagonists, adrenergic agonists and NMDA antagonists with respect to locomotor stimulatory effects in monoamine-depleted mice. Naunyn Schmiedebergs Arch Pharmacol 343: 568-573.
50. Gainetdinov R R, Bohn L M, Sotnikova T D, Cyr M, Laakso A, et al., (2003) Dopaminergic supersensitivity in G protein-coupled receptor kinase 6-deficient mice. Neuron 38: 291-303.
51. Xu F, Gainetdinov R R, Wetsel W C, Jones S R, Bohn L M, et al. (2000) Mice lacking the norepinephrine transporter are supersensitive to psychostimulants. Nat Neurosci 3: 465-471.
52. Bengel D. Murphy D L, Andrews A M, Wichems C H, Feltner D, et al. (1998) Altered brain serotonin homeostasis and locomotor insensitivity to 3,4-methylenedioxymethamphetamine ("Ecstasy") in serotonin transporter-deficient mice. Mol Pharmacol 53: 649-655.
53. Betancur C, Lepee-Lorgeoux I, Cazillis M, Accili D, Fuchs S, et al. (2001) Neurotensin gene expression and behavioral responses following administration of psychostimulants and antipsychotic drugs in dopamine D(3) receptor deficient mice. Neuropsychopharmacology 24: 170-182.
54. Coward D M, Doggett N S, Sayers A C (1977) The pharmacology of Ncarbamoyl-2-(2,6-dichlorophenyl)acetamidine hydrochloride (LON-954) a new tremorogenic agent. Arzneimittelforschung 27; 2326-2332.
55. Crawley J N, Paylor R (1997) A proposed test battery and constellations of specific behavioral paradigms to investigate the behavioral phenotypes of transgenic and knockout mice. Horm Behav 31: 197-211.
56. Konczak J, Ackermann H, Hertrich I, Spieker S, Dichgans J (1997) Control of repetitive lip and finger movements in Parkinson's disease: Influence of external timing signals and simultaneous execution on motor performance. Mov Disord 12: 665-676.
57. Lindner M D, Plone M A, Francis J M, Emerich D F (1996) Validation of a rodent model of Parkinson's Disease: Evidence of a therapeutic window for oral Sinemet. Brain Res Bull 39; 367-372.
58. Jolicoeur F B, Rivest R, Drumheller A (1991) Hypokinesia, rigidity, and tremor induced by hypothalamic 6-OHDA lesions in the rat. Brain Res Bull 26: 317-320.
59. Thomas S A, Marck B T, Palmiter R D, Matsumoto A M (1998) Restoration of norepinephrine and reversal of phenotypes in mice lacking dopamine beta-hydroxylase. J Neurochem 70: 2468-2476.
60. Cyr M, Beaulieu J M, Laakso A, Sotnikova T D, Yao W D, et al. (2003) Sustained elevation of extracellular dopamine causes motor dysfunction and selective degeneration of striatal GABAergic neurons. Proc Natl Acad Sci USA 100: 11035-11040.
61. Carlsson A (2002) Treatment of Parkinson's with L-DOPA. The early discovery phase, and a comment on current problems. J Neural Transm 109: 777-787.
62. White F J, Bednarz L M, Wachtel S R, Hjorth S, Brooderson R J (1988) Is stimulation of both D1 and D2 receptors necessary for the expression of dopamine-mediated behaviors? Pharmacol Biochem Behav 30: 189-193.
63. Sotnikova T D, Budygin E A, Jones S R, Dykstra L A, Caron M G, et al. (2004) Dopamine transporter-dependent and -independent actions of trace amine beta-phenylethylamine. J Neurochem 91: 362-373.
64. Iravani M M, Jackson M J, Kuoppamaki M, Smith L A, Jenner P (2003) 3,4-methylenedioxymethamphetamine (ecstasy) inhibits dyskinesia expression and normalizes motor activity in 1-methyl-4-phenyl-1,2,3,6-tetrahydropyridine-treated primates. J Neurosci 23: 9107-9115.
65. Fumagalli F, Gainetdinov R R, Valenzano K J, Caron M G (1998) Role of dopamine transporter in methamphetamine-induced neurotoxicity: Evidence from mice lacking the transporter. J Neurosci 18: 4861-4869.

66. Gainetdinov R R, Fumagalli F, Jones S R, Caron M G (1997) Dopamine transporter is required for in vivo MPTP neurotoxicity: Evidence from mice lacking the transporter. Neurochem 69: 1322-1325.
67. Miller G W, Gainetdinov R R, Levey A I, Caron M G (1999) Dopamine transporters and neuronal injury. Trends Pharmacol Sci 20: 424-429.
68. Colado M I, O'Shea E, Green A R (2004) Acute and long-term effects of MDMA on cerebral dopamine biochemistry and function. Psychopharmacology (Berl) 173: 249-263.
69. O'Callaghan J P, Miller D B (1994) Neurotoxicity profiles of substituted amphetamines in the C57BL/6J mouse. J Pharmacol Exp Ther 270: 741-751.
70. Bannon M J, Roth R H (1983) Pharmacology of mesocortical dopamine neurons. Pharmacol Rev 35: 53-68.
71. Greenamyre J T, Betarbet R, Sherer T B (2003) The rotenone model of Parkinson's disease: genes, environment and mitochondria. Parkinsonism Relat Disord 9 Suppl 2: S59-S64.
72. Willis G L, Kennedy G A (2004) The implementation of acute versus chronic animal models for treatment discovery in Parkinson's disease. Rev Neurosci 15: 75-87.
73. Mooslehner K A, Chan P M, Xu W, Liu L, Smadja C, et al. (2001) Mice with very low expression of the vesicular monoamine transporter 2 (gene survive into adulthood: Potential mouse model for parkinsonism. Mol Cell Biol 21: 5321-5331.
74. Chen L. Zhuang X (2003) Transgenic mouse models of dopamine deficiency. Ann Neurol 54 Suppl: S91-S102.
75. Kim D S, Palmiter R D (2003) Adenosine receptor blockade reverses hypophagia and enhances locomotor activity of dopamine-deficient mice. Proc Natl Acad Sci USA 100: 1346-1351.
76. Szczypka M S, Rainey M A, Kim D S, Alaynick W A, Marck B T, et al. (1999) Feeding behavior in dopamine-deficient mice. Proc Natl Acad Sci USA 96: 12138-12143.
77. Chartoff E H, Marck B T, Matsumoto A M, Dorsa D M, Palmiter R D (2001) Induction of stereotypy in dopamine-deficient mice requires striatal D1 receptor activation. Proc Natl Acad Sci USA 98: 10451-10456.
78. Cannon C M, Palmiter R D (2003) Reward without dopamine. J Neurosci 23: 10827-10831.
79. Denenberg V H, Kim D S, Palmiter R D (2004) The role of dopamine in learning, memory, and performance of a water escape task. Behav Brain Res 148: 73-78.
80. Chartoff E H, Heusner C L, Palmiter R D (2005) Dopamine is not required for the hyperlocomotor response to NMDA receptor antagonists. Neuropsychopharmacology 30: 1324-1333.
81. Kim D S, Szczypka M S, Palmiter R D (2000) Dopamine-deficient mice are hypersensitive to dopamine receptor agonists. J Neurosci 20: 4405-4413.
82. Beaulieu J M, Sotnikova T D, Yao W D, Kockeritz L, Woodgett J R, et al. (2004) Lithium antagonizes dopamine-dependent behaviors mediated by an AKT/glycogen synthase kinase 3 signaling cascade. Proc Natl Acad Sci USA 101: 5099-5104.
83. Gainetdinov R R, Wetsel W C, Jones S R, Levin E D, Jaber M, et al. (1999) Role of serotonin in the paradoxical calming effect of psychostimulants on hyperactivity. Science 283: 397-401.
84. Schmidt W J, Mayerhofer A, Meyer A, Kovar K A (2002) Ecstasy counteracts catalepsy in rats, an anti-parklinsonian effect? Neurosci Lett 330: 251-254.
85. Lebsanft H B, Mayerhofer A, Kovar K A, Schmidt W J (2003) Is the Ecstasy induced ipsilateral rotation in 6-hydroxydopamine unilaterally lesioned rats dopamine independent? J Neural Transm 110: 707-718.
86. Lyles S, Cadet J L (2003) Methylenedioxymethamphetamine (MDMA, Ecstasy) neurotoxicity: Cellular and molecular mechanisms. Brain Res Brain Res Rev 42: 155-168.
87. Janssen P A, Leysen J E, Megens A A, Awouters F H (1999) Does phenylethylamine act as an endogenous amphetamine in some patients? In J Neuropsychopharmcol 2: 229-240.
88. Borowsky B, Adham N, Jones K A, Raddatz X, Artymyshyn R, et al., (2001) Trace amines: Identification of a family of mammalian G protein-coupled receptors. Proc Natl Acad Sci USA 98: 8966-8971.
89. Janssen P A, Niemegeers C J, Schellekens K H (1965) Is it possible to predict the clinical effects of neuroleptic drugs (major tranquilizers) from animal data? I. "Neuroleptic activity spectra" for rats. Arzneimittelforschung 15; 104-117.

The foregoing is illustrative of the present invention, and is not to be construed as limiting thereof. The invention is defined by the following claims, with equivalents of the claims to be included therein.

What is claimed is:

1. A method of treating a subject for Parkinson's disease comprising: administering to said subject in need thereof synergistic effective amounts of L-DOPA in combination with 3,4 methylenedioxymethamghetamine (MDMA) or a pharmaceutically acceptable salt thereof.
2. The method of claim 1, wherein said MDMA is (±)-3,4 methylenedioxymethamphetamine ((±)-MDMA).
3. The method of claim 1, wherein said MDMA is (+)-3,4 methylenedioxymethamphetamine ((+)-MDMA).
4. The method of claim 1, wherein said L-DOPA is administered in combination with carbidopa.
5. The method of claim 1, wherein said treating comprises treating at least one motor symptom of Parkinson's disease.
6. The method of claim 1, wherein said Parkinson's disease is early onset Parkinson's disease.
7. The method of claim 1, wherein said Parkinson's disease is late stage Parkinson's disease.
8. The method of claim 1, wherein said subject is a human subject.
9. A method of treating a human subject in need thereof for Parkinson's disease comprising:
   administering to said subject L-DOPA in combination with carbidopa, and
   administering to said subject 3,4 methylenedioxymethamphetamine (MDMA) or a pharmaceutically acceptable salt thereof, said MDMA administered in combination with said L-DOPA in an amount effective to synergistically enhance the efficacy of said L-DOPA.
10. The method of claim 9, wherein said MDMA is (±)-3,4 methylenedioxymethamphetamine ((±)-MDMA).
11. The method of claim 9, wherein said MDMA is (+)-3,4 methylenedioxymethamphetamine ((+)-MDMA).
12. The method of claim 9, wherein said treating comprises treating at least one motor symptom of Parkinson's disease.
13. The method of claim 9, wherein said Parkinson's disease is early onset Parkinson's disease.
14. The method of claim 9, wherein said Parkinson's disease is late stage Parkinson's disease.

* * * * *

UNITED STATES PATENT AND TRADEMARK OFFICE
CERTIFICATE OF CORRECTION

PATENT NO. : 8,877,802 B2
APPLICATION NO. : 11/460046
DATED : November 4, 2014
INVENTOR(S) : Caron et al.

It is certified that error appears in the above-identified patent and that said Letters Patent is hereby corrected as shown below:

In the Claims:
Column 34, Claim 1, Line 30:
    Please correct "3,4 methylenedioxymethamghetamine(MDMA)"
        to read -- 3,4 methylenedioxymethamphetamine (MDMA) --

Page 1 of 1

Signed and Sealed this
Tenth Day of March, 2015

Michelle K. Lee
*Deputy Director of the United States Patent and Trademark Office*